(12) United States Patent
Lek et al.

(10) Patent No.: US 11,674,140 B2
(45) Date of Patent: Jun. 13, 2023

(54) COMPOSITIONS AND METHODS FOR TREATING FACIOSCAPULOHUMERAL DYSTROPHY

(71) Applicant: THE CHILDREN'S MEDICAL CENTER CORPORATION, Boston, MA (US)

(72) Inventors: Angela Lek, Boston, MA (US); Louis M. Kunkel, Boston, MA (US)

(73) Assignee: THE CHILDREN'S MEDICAL CENTER CORPORATION, Boston, MA (US)

( * ) Notice: Subject to any disclaimer, the term of this patent is extended or adjusted under 35 U.S.C. 154(b) by 62 days.

(21) Appl. No.: 16/643,772

(22) PCT Filed: Sep. 7, 2018

(86) PCT No.: PCT/US2018/050043
§ 371 (c)(1),
(2) Date: Mar. 2, 2020

(87) PCT Pub. No.: WO2019/051290
PCT Pub. Date: Mar. 14, 2019

(65) Prior Publication Data
US 2021/0163931 A1    Jun. 3, 2021

Related U.S. Application Data

(60) Provisional application No. 62/555,599, filed on Sep. 7, 2017.

(51) Int. Cl.
| | |
|---|---|
| *C12N 15/113* | (2010.01) |
| *A61P 21/00* | (2006.01) |
| *A61K 31/366* | (2006.01) |
| *A61K 31/395* | (2006.01) |
| *A61K 31/436* | (2006.01) |
| *A61K 31/5377* | (2006.01) |
| *C12N 15/10* | (2006.01) |

(52) U.S. Cl.
CPC .......... *C12N 15/113* (2013.01); *A61K 31/366* (2013.01); *A61K 31/395* (2013.01); *A61K 31/436* (2013.01); *A61K 31/5377* (2013.01); *A61P 21/00* (2018.01); *C12N 15/1093* (2013.01); *C12N 15/1137* (2013.01); *C12N 2310/3233* (2013.01)

(58) Field of Classification Search
CPC .. A61K 31/00; A61K 2121/00; C12N 15/113; C12N 2310/11; C12N 2310/321; C12N 2310/322; A61P 21/00

USPC ...... 424/9.1; 435/6.1, 91.1, 91.31, 455, 458; 530/300, 350; 514/44 A, 44 R
See application file for complete search history.

(56) References Cited

U.S. PATENT DOCUMENTS

| | | | |
|---|---|---|---|
| 2014/0242093 A1* | 8/2014 | Tapscott | A61K 38/1709 424/172.1 |
| 2019/0024083 A1* | 1/2019 | Harper | A61P 21/00 |

FOREIGN PATENT DOCUMENTS

| | | | | |
|---|---|---|---|---|
| WO | WO-2017050836 A1 | * | 3/2017 | ........... C12N 15/113 |
| WO | WO-2018057863 A1 | * | 3/2018 | ............. A61P 21/00 |

OTHER PUBLICATIONS

Vanderplanck et al (PLos One, vol. 6, Issue 10, e26820, pp. 1-14 (2011)) (Year: 2011).*
Davidovic et al (PLOS Genetics, vol. 9, Issue 3, e1003367, pp. 1-16 (2013)), (Year: 2013).*
Wettersten et al (Cancer Biol. & Therapy, vol. 14, pp. 278-285 (2013)) (Year: 2013).*
Uchiyama et al (Arterioscler Thromb Vasc Biol., pp. 1155-1161 (Apr. 2000)). (Year: 2000).*
Bosnakovski et al (Disease Models and Mechanisms, vol. 10, pp. 1211-1216 (2017)) (Year: 2017).*
Bosnakovski et al (The EMBO J., vol. 27, pp. 2766-2779 (2008)) (Year: 2008).*
Uehara et al (Methods Enzymol. vol. 201, p. 370 (1991)) (Year: 1991).*
Fukazawa et al (Biochem. Pharmacol. vol. 42, p. 1661 (1991)). (Year: 1991).*
Bosnakovski et al., "p53-Independent DUX4 Pathology in Cell and Animal Models of Facioscapulohumeral Muscular Dystrophy," Disease Models and Mechanisms, Jul. 26, 2017; vol. 10, pp. 1211-1216.
Campbell et al., "BET Bromodomain Inhibitors and Agonists of the Beta-2 Adrenergic Receptor Identified in Screens for Compounds that Inhibit DUX4 Expression in FSHD Muscle Cells," Skeletal Muscle, Sep. 4, 2017; vol. 7, No. 16, pp. 1-18.
Davidovic et al., "A Novel Role for the RNA-Binding Protein FXR1P in Myoblasts Cell-Cycle Progression by Modulating p21/Cdkn1a/Cip1/Waf1 mRNA Stability," PLOS Genetics, Mar. 21, 2013; vol. 9, No. 3, e1003367.
Tawil et al., "Clinical Trial Preparedness in Facioscapulohumeral Muscular Dystrophy: Clinical, Tissue, and Imaging Outcome Measures, May 29-30, 2015, Rochester, New York," Neuromuscular Disorders, Nov. 9, 2015; vol. 26, pp. 181-186.

(Continued)

*Primary Examiner* — Jane J Zara
(74) *Attorney, Agent, or Firm* — Melissa Hunter-Ensor; Greenberg Traurig, LLP

(57) ABSTRACT

Compositions and methods for treating FSHD and for identifying agents useful for the treatment of FSHD.

1 Claim, 37 Drawing Sheets

(56) References Cited

OTHER PUBLICATIONS

Wettersten et al., "A Novel p21 Attenuator Which Is Structurally Related to Sorafenib," Cancer Biology & Therapy, Mar. 2013; vol. 14, No. 3, pp. 278-285.
International Search Report and Written Opinion for corresponding PCT Patent Application No. PCT/US18/50043, dated Jan. 29, 2019 (17 pages).
Mitsuhashi et al., "Expression of DUX4 in zebrafish development recapitulates facioscapulohumeral muscular dystrophy," Human Molecular Genetics, 2013, vol. 22, No. 3, pp. 568-577.

* cited by examiner

FSHD is linked to a truncated repetitive region in the subtelomeric region of chromosome 4
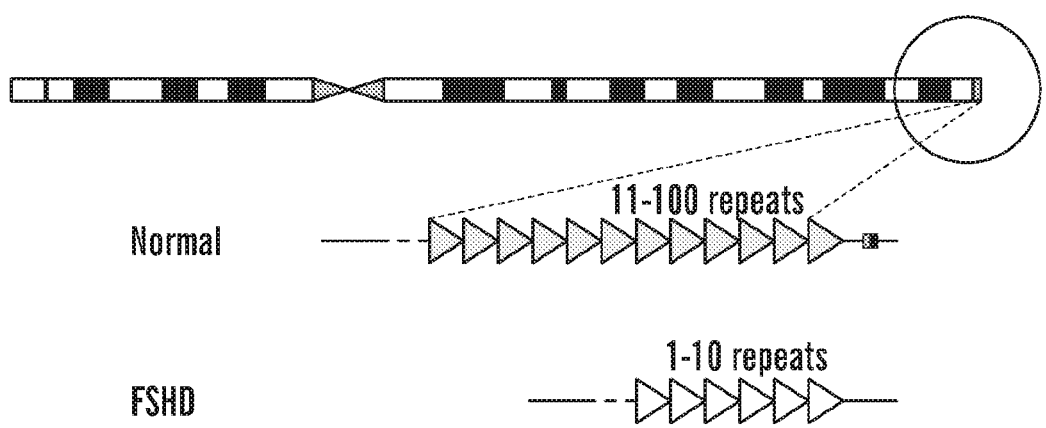
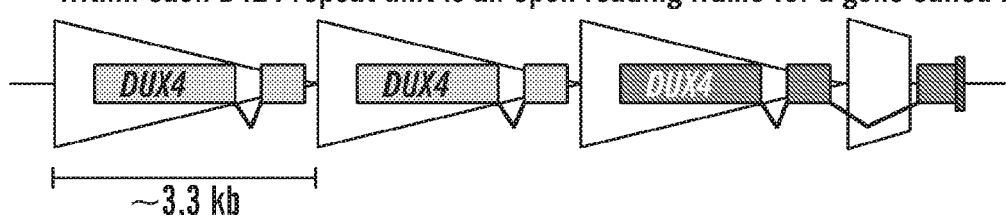
Within each D4Z4 repeat unit is an open reading frame for a gene called DUX4
*FIG. 1H*

Top: Wallace, L (2012) Molecular Therapy. Bottom: Bosnakovski, D (2014) Skeletal Muscle

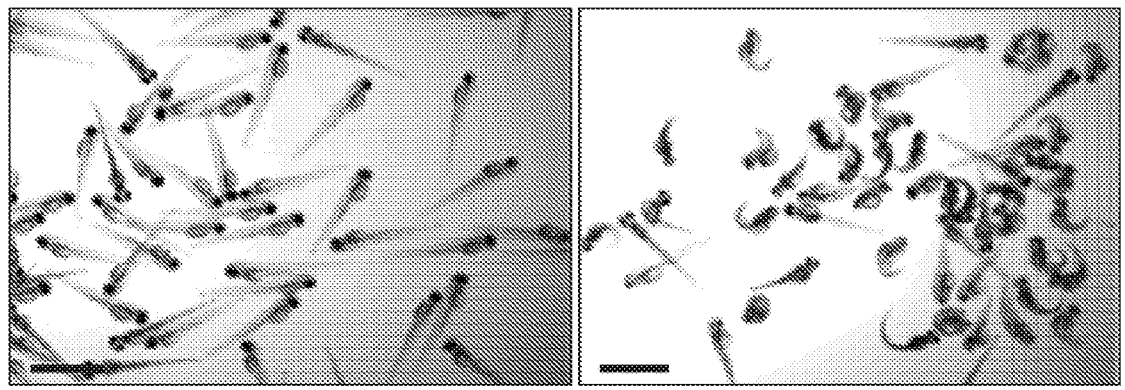
FIG. 1N-A
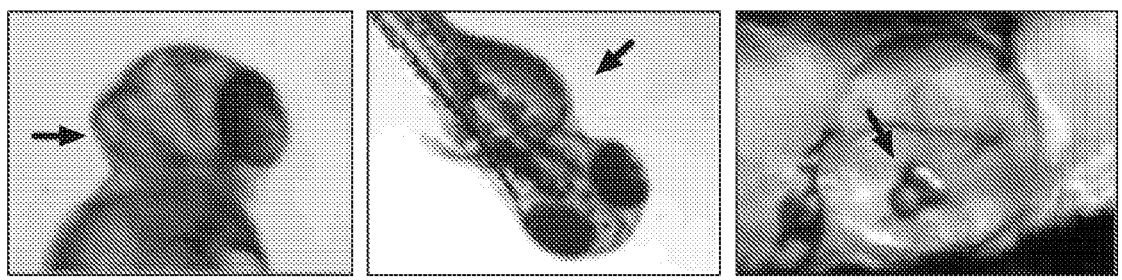
FIG. 1N-B
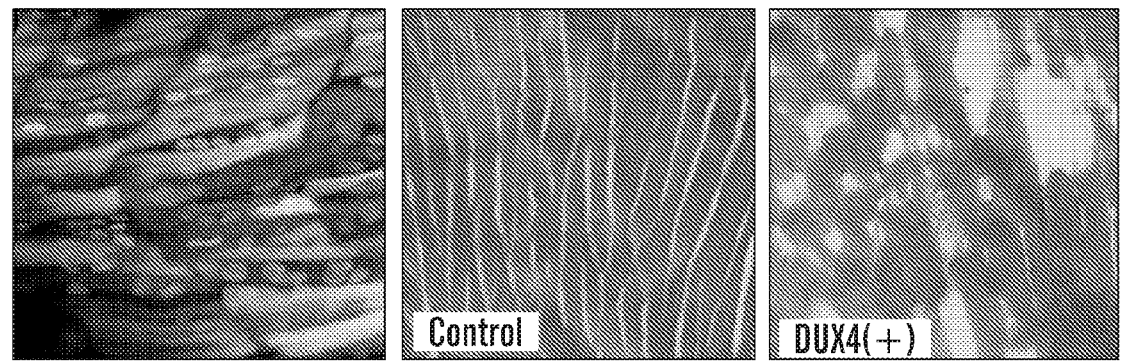
FIG. 1N-C

Loss-of-function CRISPR screen in HEK293T cells

| Experiment 5 | | | |
|---|---|---|---|
| Rank | Gene | p-value | sgRNA |
| 1 | EXTL3 | 2.26E-07 | 5 |
| 2 | B3GAT3 | 9.27E-06 | 6 |
| 3 | FAAH | 2.01E-05 | 6 |
| 4 | hsa-mir-3652 | 2.37E-05 | 4 |
| 5 | OLFM2 | 5.63E-05 | 5 |
| 6 | RCOR3 | 8.12E-05 | 2 |
| 7 | SLC35B2 | 0.00011178 | 5 |
| 8 | RPRML | 0.00011916 | 1 |
| 9 | SOX12 | 0.00020643 | 4 |
| 11 | PPFIA1 | 0.00026748 | 5 |
| 12 | TMEM165 | 0.00029506 | 4 |
| 13 | C2orf78 | 0.00031632 | 1 |
| 15 | KLHL5 | 0.00031767 | 3 |
| 16 | NLGN2 | 0.00031993 | 5 |
| 17 | SPRY4 | 0.00033169 | 2 |
| 18 | SMARCA4 | 0.00038641 | 2 |
| 19 | CSNK1D | 0.00040088 | 4 |
| 20 | hsa-mir-5186 | 0.00041761 | 4 |

| Rank | Gene | p-value | sgRNA |
|---|---|---|---|
| 1 | EXTL3 | 2.49E-06 | 5 |
| 2 | SLC35D1 | 7.01E-06 | 5 |
| 3 | B3GAT3 | 4.36E-05 | 4 |
| 4 | SLC35B2 | 8.03E-05 | 4 |
| 5 | CCDC181 | 9.11E-05 | 1 |
| 6 | EXT2 | 0.00010423 | 4 |
| 7 | PIGP | 0.00013724 | 4 |
| 8 | MYL7 | 0.00025663 | 1 |
| 9 | hsa-mir-3915 | 0.00028557 | 3 |
| 11 | GCSAML | 0.00030094 | 3 |
| 12 | HEATR6 | 0.00035521 | 3 |
| 13 | HOXA3 | 0.00040495 | 1 |
| 15 | B4GALT7 | 0.00044836 | 2 |
| 16 | TMED10 | 0.00047549 | 2 |
| 17 | CDC14A | 0.00049403 | 3 |
| 18 | ABI3BP | 0.00052795 | 2 |
| 19 | ADAMTS15 | 0.00054468 | 2 |
| 20 | SASH1 | 0.00038143 | 3 |

| Rank | Gene | p-value | sgRNA |
|---|---|---|---|
| 1 | EXTL3 | 2.26E-07 | 5 |
| 2 | SLC35B2 | 2.26E-07 | 4 |
| 3 | NDST1 | 2.26E-07 | 4 |
| 4 | EXT1 | 1.13E-06 | 3 |
| 5 | SLC35D1 | 1.58E-06 | 4 |
| 6 | UNC50 | 2.94E-06 | 3 |
| 7 | FABP6 | 1.20E-05 | 3 |
| 8 | B3GAT3 | 1.97E-05 | 4 |
| 9 | ASB13 | 3.55E-05 | 5 |
| 11 | NR1I2 | 7.98E-05 | 3 |
| 12 | TMEM165 | 0.00010966 | 3 |
| 13 | PRPH2 | 0.00012594 | 4 |
| 15 | CNTFR | 0.00016528 | 4 |
| 16 | PRSS22 | 0.00017342 | 4 |
| 17 | SPATA32 | 0.00021638 | 4 |
| 18 | PACSIN3 | 0.00021864 | 3 |
| 19 | B4GALT7 | 0.00023221 | 3 |
| 20 | RASGRP1 | 0.00027607 | 2 |

*FIG. 6*

Loss-of-function CRISPR screen in MB135 immortalized human myoblast line

MB135 screen 1

| Gene | p-value | Rank | sgRNA count |
|---|---|---|---|
| NF2 | 2.26E-07 | 5 | 5 |
| ZCCHC14 | 2.26E-07 | 4 | 5 |
| HIF1A | 2.26E-07 | 2 | 5 |
| ARNT | 2.26E-07 | 1 | 6 |
| CREBBP | 2.26E-07 | 3 | 6 |
| LATS2 | 1.13E-06 | 6 | 6 |
| TADA2B | 2.49E-06 | 7 | 5 |
| TAOK1 | 2.94E-06 | 8 | 5 |
| AMOTL2 | 2.94E-06 | 9 | 4 |
| TAF5L | 7.01E-06 | 10 | 6 |
| MED25 | 1.20E-05 | 11 | 4 |
| MED16 | 1.51E-05 | 12 | 5 |
| ATXN7 | 1.70E-05 | 13 | 6 |
| DEK | 2.60E-05 | 14 | 3 |
| CDK17 | 2.92E-05 | 15 | 5 |
| TP53 | 3.01E-05 | 16 | 4 |
| MED24 | 4.45E-05 | 17 | 6 |
| SPOP | 5.72E-05 | 18 | 5 |
| TADA1 | 9.29E-05 | 19 | 5 |
| CAND1 | 0.00011644 | 20 | 4 |

MB135 screen 2

| Gene | p-value | Rank | sgRNA count |
|---|---|---|---|
| ZCCHC14 | 1.58E-06 | 1 | 6 |
| HIF1A | 4.30E-06 | 2 | 4 |
| MED16 | 9.27E-06 | 3 | 4 |
| MED24 | 1.06E-05 | 4 | 5 |
| ARNT | 1.97E-05 | 5 | 5 |
| MED25 | 5.68E-05 | 6 | 4 |
| PCDHB10 | 9.84E-05 | 7 | 2 |
| THAP3 | 0.00012096 | 8 | 4 |
| HSD17B3 | 0.00014357 | 9 | 6 |
| UCP3 | 0.00019829 | 10 | 3 |
| ACY1 | 0.00020417 | 11 | 2 |
| TADA1 | 0.00025663 | 12 | 5 |
| POLRMT | 0.00028059 | 13 | 6 |
| PHF12 | 0.0003136 | 14 | 5 |
| NACA | 0.00032807 | 15 | 4 |
| DOT1L | 0.00033757 | 16 | 4 |
| DBP | 0.00037239 | 17 | 1 |
| SH3BP1 | 0.00056729 | 18 | 4 |
| TADA2B | 0.00056865 | 19 | 5 |
| PTRHD1 | 0.00057407 | 20 | 5 |

*FIG. 7*

DUX4 expression via baculovirus
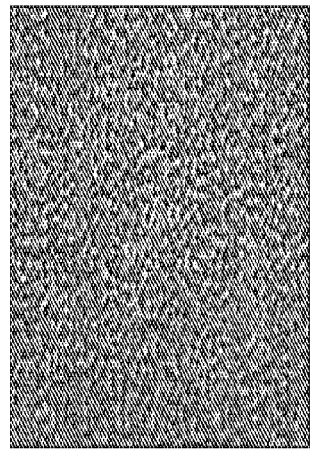
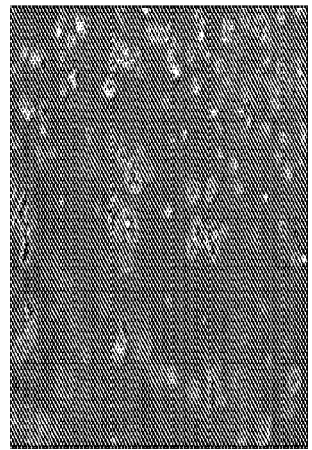
DUX4 expression via doxycyline induction:
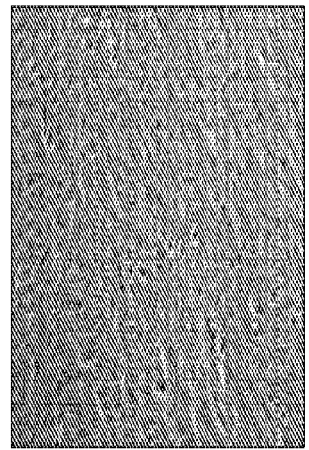
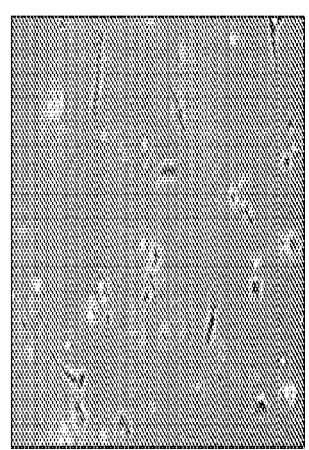
*FIG. 8A*  *FIG. 8B*

Caspase-3/7 cleavage of the luminogenic substrate containing the DEVD sequence. Following caspase cleavage, a substrate for luciferase (aminoluciferin) is released, resulting in the luciferase reaction and the production of light.

COMPOSITIONS AND METHODS FOR TREATING FACIOSCAPULOHUMERAL DYSTROPHY

CROSS-REFERENCE TO RELATED APPLICATION

This application is the U.S. national phase application, pursuant to 35 U.S.C. § 371, of PCT International Application Ser. No.: PCT/US2018/050043, filed Sep. 7, 2018, designating the United States and published in English, which claims the benefit of the following U.S. Provisional Application No.: 62/555,599, filed Sep. 7, 2017, the entire contents of which are incorporated herein by reference.

BACKGROUND OF THE INVENTION

Facioscapulohumeral dystrophy (FSHD) is the most common autosomal dominant form of muscular dystrophy affecting 1 in 8000 individuals worldwide. Disease onset is variable, with the majority manifesting symptoms in their second decade, while others remaining asymptomatic into late adulthood. FSHD is uniquely characterized by an asymmetric pattern of weakness involving the facial, shoulder and upper arm muscles. In addition to muscular dystrophy, a fraction of FSHD patients experience hearing and vision loss. Unlike 'classical' forms of muscular dystrophy arising from single gene loss-of-function mutations, the genetics of FSHD is complex and is not entirely solved. Currently, the most widely accepted model implicates misexpression of double homeobox 4 (DUX4), a double homeobox transcription factor normally silenced in somatic tissue, in the disease pathogenesis. Compared to unaffected individuals, FSHD patients express significantly higher levels of DUX4 full-length (DUX4-FL) protein in their skeletal muscle. DUX4 expression is known to be highly toxic, causing cell death within 48 hours post-transfection, and lethality when expressed during embryonic development in zebrafish and mice. As a germ-line transcription factor, DUX4 misexpression in the somatic cell is thought to activate a transcriptional cascade of gene programs associated with early stem-cell programs in post-mitotic cells. Genes in this class such as zinc finger and SCAN domain containing 4 (ZSCAN4), PRAME family member 1 (PRAMEF1), SPRY domain-containing protein 5 (SPRYD5), and methyl-CpG binding domain protein 3-like 2 (MDB3L2) are known to be dramatically up-regulated in response to DUX4 ectopic expression, and are routinely used as FSHD biomarkers to assess disease pathogenesis in patients and animal models. It is therefore likely that dysregulation of DUX4 target genes and their downstream networks play a role in FSHD, and that their identification will greatly enhance our understanding of the disease pathogenesis. Evidence of DUX4 misexpression in FSHD is compelling, given the exclusive linkage of FSHD with permissive alleles that give rise to a stable DUX4 transcript. However, there is mounting clinical evidence that DUX4 expression is not an exclusive determinant of FSHD pathology, prompting the search for the missing 'second hit'. Firstly, FSHD disease onset, severity and prognosis is extremely variable, even between affected members of the same family sharing the equivalent D4Z4 repeat contraction. Furthermore, if DUX4 expression is linked to FSHD, why is there no correlation between levels of DUX4 transcript or protein expression with clinical severity? Most confounding is evidence that rare unaffected individuals with greater than 100 D4Z4 units and full muscle strength can express DUX4 in both their skeletal muscle and myogenic cells.

The current understanding of FSHD is incomplete and no cure exists exists for this progressive disease. Improved methods for treating FSHD are urgently required.

SUMMARY OF THE INVENTION

As described below, the present invention features compositions and methods for treating FSHD and for identifying agents useful for the treatment of FSHD.

In one aspect, the invention features a method for treating FSHD, the method involving administering to a patient having or having a propensity to develop FSHD, an agent that reduces the expression or activity of a hypoxia response pathway protein (e.g., of cyclin dependent kinase inhibitor 1A (CDKN1A), hypoxia-inducible factor 1-alpha (HIF1A), hypoxia-inducible factor 1-beta (HIF1B), aryl hydrocarbon receptor nuclear translocator (ARNT), CREB binding protein (CREBBP), CBP, and zinc finger CCHC-type containing 14 (ZCCHC14)).

In another aspect, the method for treating FSHD, the method comprising administering to a patient having or having a propensity to develop FSHD, an agent that reduces the expression or activity of a hypoxia response pathway protein that is any one or more of cyclin dependent kinase inhibitor 1A (CDKN1A), hypoxia-inducible factor 1-alpha (HIF1A), hypoxia-inducible factor 1-beta (HIF1B), aryl hydrocarbon receptor nuclear translocator (ARNT), CREB binding protein (CREBBP), CBP, and zinc finger CCHC-type containing 14 (ZCCHC14).

In some embodiments of these methods, the agent is a small compound, inhibitory nucleic acid molecule, polypeptide, or a fragment thereof. In some embodiments, the agent is a small compound that is a p21 inhibitor, Hif1a inhibitor, PI3K inhibitor, tyrosine kinase inhibitor, protein kinase C inhibitor, MAPK inhibitor, mTOR inhibitor, inhibitor of Redox signaling, inhibitor of glucokinase. In other embodiments, the agent is Herbimycin A, Herceptin, Iressa, calphostin C, wortmannin, LY294002, PD98059, rapamycin, diphenylene iodonium, mannoheptulose, UC2288, 4-Chloro-3-(trifluoromethyl)phenyl isocyanate (CAS 327-78-6), Sterigmatocystin, Chetomin, Cryptotanshione, EF-24, FM19G11, and PX 12. In some embodiments the agent is an inhibitory nucleic acid molecule that is an antisense nucleic acid molecule, siRNA, shRNA, or a modified form thereof. In some embodiments, modified inhibitory nucleic acid molecule includes a morpholino.

Another aspect of the invention provides a method for identifying a genetic modifier of DUX4 toxicity, and the method includes editing each gene in a genome of a cell population using a Clustered Regularly Interspaced Short Palindromic Repeat (CRISPR) library; overexpressing DUX4 in the gene-edited cell population; growing the cells under conditions that allow DUX4 resistant cells to survive or proliferate; and isolating genomic DNA from the cells, thereby identifying a genetic modifier of DUX4 toxicity. In one embodiment of this method, the library is a knock-out or upregulation library.

Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "EF-24" is meant (3E,5E)-3,5-bis[(2-fluorophenyl)methylene]-4-piperidinone, and its structure is provided below:

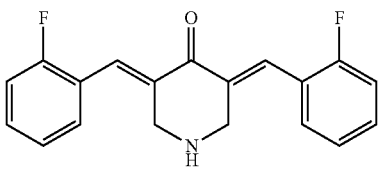 [SMILES: O=C1/C(=C/c2ccccc2F)CNC/C1=C\c1ccccc1F]

The term "FM19G11" refers to a particular HIFα inhibitor. Its structure is provided below:

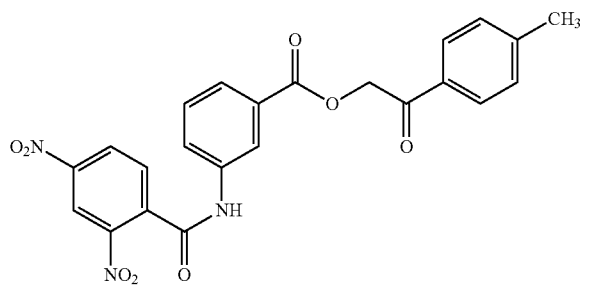 [SMILES: Cc1ccc(C(=O)COC(=O)c2cccc(NC(=O)c3ccc([N+](=O)[O-])cc3[N+](=O)[O-])c2)cc1]

By "hypoxia inducible factor (HIF)" is meant a heterodimeric transcription factor composed of an HIF-α subunit and an HIF-β subunit also known as the aryl hydrocarbon receptor nuclear translocator.

By "Hypoxia-inducible factor 1-alpha isoform (Hif1 alpha)" is meant the alpha subunit of the HIF1 protein. An exemplary HIF1 alpha amino acid sequence is provided at Uniprot.org under Accession No. Q16665, which is reproduced below.

```
>sp|Q16665|HIF1A_HUMAN Hypoxia-inducible
factor 1-alpha OS = Homo sapiens GN = HIF1A
PE = 1 SV = 1
MEGAGGANDKKKISSERRKEKSRDAARSRRSKESEVFYELAHQLP

LPHNVSSHLDKASVMRLTISYLRVRKLLDAGDLDIEDDMKAQMNC

FYLKALDGFVMVLTDDGDMIYISDNVNKYMGLTQFELTGHSVFDF

THPCDHEEMREMLTHRNGLVKKGKEQNTQRSFFLRMKCTLTSRGR

TMNIKSATWKVLHCTGHIHVYDTNSNQPQCGYKKPPMTCLVLICE

PIPHPSNIEIPLDSKTFLSRHSLDMKFSYCDERITELMGYEPEEL

LGRSIYEYYHALDSDHLTKTHHDMFTKGQVTTGQYRMLAKRGGYV

WVETQATVIYNTKNSQPQCIVCVNYVVSGIIQHDLIFSLQQTECV

LKPVESSDMKMTQLFTKVESEDTSSLFDKLKKEPDALTLLAPAAG

DTIISLDFGSNDTETDDQQLEEVPLYNDVMLPSPNEKLQNINLAM

SPLPTAETPKPLRSSADPALNQEVALKLEPNPESLELSFTMPQIQ

DQTPSPSDGSTRQSSPEPNSPSEYCFYVDSDMVNEFKLELVEKLF

AEDTEAKNPFSTQDTDLDLEMLAPYIPMDDDFQLRSFDQLSPLES

SSASPESASPQSTVTVFQQTQIQEPTANATTTTATTDELKTVTKD

RMEDIKILIASPSPTHIHKETTSATSSPYRDTQSRTASPNRAGKG

VIEQTEKSHPRSPNVLSVALSQRTTVPEEELNPKILALQNAQRKR

KMEHDGSLFQAVGIGTLLQQPDDHAATTSLSWKRVKGCKSSEQNG

MEQKTIILIPSDLACRLLGQSMDESGLPQLTSYDCEVNAPIQGSR

NLLQGEELLRALDQVN
```

By "Hif1 alpha polynucleotide sequence" is meant the sequence encoding a Hif1 alpha polypeptide or fragment thereof. An exemplary sequence is provided below:

```
>NM_001243084.1 Homo sapiens hypoxia inducible factor 1 alpha subunit
(HIF1A), transcript variant 3, mRNA
ATTTGAAAACTTGGCAACCTTGGATTGGATGGATTCATATTTCTTAGTATAGAAGTTCTTGATATAACTG

AAAAATTAAGTTAAACACTTAATAAGTGGTGGTTACTCAGCACTTTTAGATGCTGTTTATAATAGATGAC

CTTTTCTAACTAATTTACAGTTTTTTGAAAGATAACTGAGAGGTTGAGGGACGGAGATTTTCTTCAAGCA

ATTTTTTTTTCATTTTAAATGAGCTCCCAATGTCGGAGTTTGGAAAACAAATTTGTCTTTTTAAAAGAA

GGTCTAGGAAACTCAAAACCTGAAGAATTGGAAGAAATCAGAATAGAAAATGGTAGGATAAGTTCTGAAC

GTCGAAAAGAAAAGTCTCGAGATGCAGCCAGATCTCGGCGAAGTAAAGAATCTGAAGTTTTTTATGAGCT

TGCTCATCAGTTGCCACTTCCACATAATGTGAGTTCGCATCTTGATAAGGCCTCTGTGATGAGGCTTACC

ATCAGCTATTTGCGTGTGAGGAAACTTCTGGATGCTGGTGATTTGGATATTGAAGATGACATGAAAGCAC

AGATGAATTGCTTTTATTTGAAAGCCTTGGATGGTTTTGTTATGGTTCTCACAGATGATGGTGACATGAT

TTACATTTCTGATAATGTGAACAAATACATGGGATTAACTCAGTTTGAACTAACTGGACACAGTGTGTTT

GATTTTACTCATCCATGTGACCATGAGGAAATGAGAGAAATGCTTACACACAGAAATGGCCTTGTGAAAA

AGGGTAAAGAACAAAACACACAGCGAAGCTTTTTTCTCAGAATGAAGTGTACCCTAACTAGCCGAGGAAG
```

-continued

```
AACTATGAACATAAAGTCTGCAACATGGAAGGTATTGCACTGCACAGGCCACATTCACGTATATGATACC

AACAGTAACCAACCTCAGTGTGGGTATAAGAAACCACCTATGACCTGCTTGGTGCTGATTTGTGAACCCA

TTCCTCACCCATCAAATATTGAAATTCCTTTAGATAGCAAGACTTTCCTCAGTCGACACAGCCTGGATAT

GAAATTTTCTTATTGTGATGAAAGAATTACCGAATTGATGGGATATGAGCCAGAAGAACTTTTAGGCCGC

TCAATTTATGAATATTATCATGCTTTGGACTCTGATCATCTGACCAAAACTCATCATGATATGTTTACTA

AAGGACAAGTCACCACAGGACAGTACAGGATGCTTGCCAAAAGAGGTGGATATGTCTGGGTTGAAACTCA

AGCAACTGTCATATATAACACCAAGAATTCTCAACCACAGTGCATTGTATGTGTGAATTACGTTGTGAGT

GGTATTATTCAGCACGACTTGATTTTCTCCCTTCAACAAACAGAATGTGTCCTTAAACCGGTTGAATCTT

CAGATATGAAAATGACTCAGCTATTCACCAAAGTTGAATCAGAAGATACAAGTAGCCTCTTTGACAAACT

TAAGAAGGAACCTGATGCTTTAACTTTGCTGGCCCCAGCCGCTGGAGACACAATCATATCTTTAGATTTT

GGCAGCAACGACACAGAAACTGATGACCAGCAACTTGAGGAAGTACCATTATATAATGATGTAATGCTCC

CCTCACCCAACGAAAAATTACAGAATATAAATTTGGCAATGTCTCCATTACCCACCGCTGAAACGCCAAA

GCCACTTCGAAGTAGTGCTGACCCTGCACTCAATCAAGAAGTTGCATTAAAATTAGAACCAAATCCAGAG

TCACTGGAACTTTCTTTTACCATGCCCCAGATTCAGGATCAGACACCTAGTCCTTCCGATGGAAGCACTA

GACAAAGTTCACCTGAGCCTAATAGTCCCAGTGAATATTGTTTTTATGTGGATAGTGATATGGTCAATGA

ATTCAAGTTGGAATTGGTAGAAAAACTTTTTGCTGAAGACACAGAAGCAAAGAACCCATTTTCTACTCAG

GACACAGATTTAGACTTGGAGATGTTAGCTCCCTATATCCCAATGGATGATGACTTCCAGTTACGTTCCT

TCGATCAGTTGTCACCATTAGAAAGCAGTTCCGCAAGCCCTGAAAGCGCAAGTCCTCAAAGCACAGTTAC

AGTATTCCAGCAGACTCAAATACAAGAACCTACTGCTAATGCCACCACTACCACTGCCACCACTGATGAA

TTAAAAACAGTGACAAAAGACCGTATGGAAGACATTAAAATATTGATTGCATCTCCATCTCCTACCCACA

TACATAAAGAAACTACTAGTGCCACATCATCACCATATAGAGATACTCAAAGTCGGACAGCCTCACCAAA

CAGAGCAGGAAAAGGAGTCATAGAACAGACAGAAAAATCTCATCCAAGAAGCCCTAACGTGTTATCTGTC

GCTTTGAGTCAAAGAACTACAGTTCCTGAGGAAGAACTAAATCCAAAGATACTAGCTTTGCAGAATGCTC

AGAGAAAGCGAAAAATGGAACATGATGGTTCACTTTTTCAAGCAGTAGGAATTGGAACATTATTACAGCA

GCCAGACGATCATGCAGCTACTACATCACTTTCTTGGAAACGTGTAAAAGGATGCAAATCTAGTGAACAG

AATGGAATGGAGCAAAAGACAATTATTTTAATACCCTCTGATTTAGCATGTAGACTGCTGGGGCAATCAA

TGGATGAAAGTGGATTACCACAGCTGACCAGTTATGATTGTGAAGTTAATGCTCCTATACAAGGCAGCAG

AAACCTACTGCAGGGTGAAGAATTACTCAGAGCTTTGGATCAAGTTAACTGAGCTTTTTCTTAATTTCAT

TCCTTTTTTTGGACACTGGTGGCTCATTACCTAAAGCAGTCTATTTATATTTTCTACATCTAATTTTAGA

AGCCTGGCTACAATACTGCACAAACTTGGTTAGTTCAATTTTGATCCCCTTTCTACTTAATTTACATTAA

TGCTCTTTTTTAGTATGTTCTTTAATGCTGGATCACAGACAGCTCATTTTCTCAGTTTTTTGGTATTTAA

ACCATTGCATTGCAGTAGCATCATTTTAAAAAATGCACCTTTTTATTTATTTATTTTTGGCTAGGGAGTT

TATCCCTTTTTCGAATTATTTTTAAGAAGATGCCAATATAATTTTTGTAAGAAGGCAGTAACCTTTCATC

ATGATCATAGGCAGTTGAAAAATTTTTACACCTTTTTTTTCACATTTTACATAAATAATAATGCTTTGCC

AGCAGTACGTGGTAGCCACAATTGCACAATATATTTTCTTAAAAAATACCAGCAGTTACTCATGGAATAT

ATTCTGCGTTTATAAAACTAGTTTTTAAGAAGAAATTTTTTTTGGCCTATGAAATTGTTAAACCTGGAAC

ATGACATTGTTAATCATATAATAATGATTCTTAAATGCTGTATGGTTTATTATTTAAATGGGTAAAGCCA

TTTACATAATATAGAAAGATATGCATATATCTAGAAGGTATGTGGCATTTATTTGGATAAAATTCTCAAT

TCAGAGAAATCATCTGATGTTTCTATAGTCACTTTGCCAGCTCAAAAGAAAACAATACCCTATGTAGTTG

TGGAAGTTTATGCTAATATTGTGTAACTGATATTAAACCTAAATGTTCTGCCTACCCTGTTGGTATAAAG

ATATTTTGAGCAGACTGTAAACAAGAAAAAAAAAATCATGCATTCTTAGCAAAATTGCCTAGTATGTTAA
```

-continued

```
TTTGCTCAAAATACAATGTTTGATTTTATGCACTTTGTCGCTATTAACATCCTTTTTTTCATGTAGATTT

CAATAATTGAGTAATTTTAGAAGCATTATTTTAGGAATATATAGTTGTCACAGTAAATATCTTGTTTTTT

CTATGTACATTGTACAAATTTTTCATTCCTTTTGCTCTTTGTGGTTGGATCTAACACTAACTGTATTGTT

TTGTTACATCAAATAAACATCTTCTGTGGACCAGGC
```

By "Hif1 beta" also termed the "aryl hydrocarbon receptor nuclear translocator" is meant the beta subunit of the heterodimeric transcription factor, hypoxia-inducible factor 1(HIF1).

By "Hif1 alpha inhibitor" is meant an agent that inhibits Hif1 alpha expression or activity. Exemplary Hif1 alpha inhibitors include Herbimycin A, Chetomin, Cryptotanshione, EF-24, FM19G11, and PX 12, all of which are commercially available (e.g., Sigma Aldrich). One exemplary HIF-1 Inhibitor (CAS 934593-90-5) is commercially available from Millipore Sigma. The structure of methyl 3-[[2-[4-(2-adamantyl)phenoxy]acetyl]amino]-4-hydroxybenzoate is provided below:

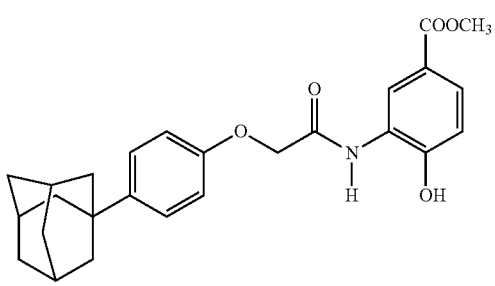 [SMILES: COC(=O)c1ccc(O)c(NC(=O)COc2ccc(C34CC5CC(CC(C5)C3)C4)cc2)c1]

By "hypoxia response pathway" is meant the genes and proteins whose expression, or activity changes in response to oxygen availability. Such changes are mediated, at least in part, via induction of hypoxia-inducible transcription factors. Exemplary members of a hypoxia response pathway include Hif1alpha, ARNT/HIF1beta, CDKN1A, p21, CREBBP, CBP, and ZCCHC14.

By "Ly294002" is meant an agent that inhibits phosphoinositide-3 kinases (PI3Ks). The structure of Ly294002 is provided below:

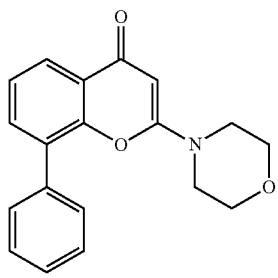 [SMILES: O=c1cc(N2CCOCC2)oc2c(-c3ccccc3)cccc12]

By "p21 inhibitor" is meant an agent that inhibits p21 expression or activity. Exemplary p21 inhibitors include UC2288 (EMD Millipore 532813), 4-Chloro-3-(trifluoromethyl)phenyl isocyanate (CAS 327-78-6) and Sterigmatocystin, both of which are commercially available from Santa Cruz. The structure of UC2288 is provided below:

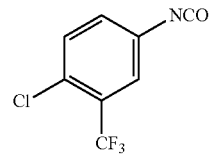

By "PD98059" is meant an MEK inhibitor that specifically inhibits MEK-1-mediated activation of MAPK. The structure of PD98059 is provided below:

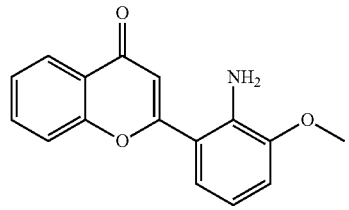 [SMILES: COc1cccc(-c2cc(=O)c3ccccc3o2)c1N]

By "PX 12" is meant 1-methylpropyl 2-imidazolyl disulfide, which downregulates HIFα. Its structure is provided below:

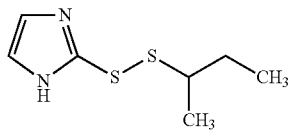

By "Facioscapulohumeral dystrophy (FSHD)" is meant FSHD type 1 or type 2. FSHD1 and 2 are genetic disorders. About eighty percent of FSHD2 is caused by the inheritance of two independent genetic variations: a heterozygous loss-of-function mutation in the encoding Structural Maintenance of Chromosomes flexible Hinge Domain containing 1 (SMCHD1) gene combined with the 4qA allele carrying the DUX4 polyadenylation site (see FSHD1), making this allele permissive to expression of the toxic DUX4 gene.

By "agent" is meant a peptide, nucleic acid molecule, or small compound.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include Facioscapulohumeral dystrophy (FSHD) (e.g., FSHD1, FSHD2) or other forms or muscular dystrophy.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder. Exemplary markers that can be used for the assessment of FSHD include MDL3L3, TRIM43, and ZSCAN4.

As used herein, "obtaining" as in "obtaining an agent" includes synthesizing, purchasing, or otherwise acquiring the agent.

By "reduces" is meant a negative alteration of at least 10%, 25%, 50%, 75%, or 100%.

By "reference" is meant a standard or control condition.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A-1N show the clinical, histopathological and molecular evidence for asymptomatic/non-manifesting carriers of FSHD.

FIG. 1A is a photograph of a non-manifesting subject with D4Z4 contraction demonstrating no facial weakness.

FIG. 1H is a schematic diagram showing that FSHD is linked to a truncated repetitive region (DZ4 repeat) in the subtelomeric region of chromosome 4. Within each DZ4 repeat is a DUX4 open reading frame.

FIG. 1N provides images obtained of DUX4 zebrafish models of FSHD. FIG. 1N-A provides an image of zebrafish after microinjection of human DUX4 mRNA into zebrafish embryos that results in a mutant phenotype (right) compared to uninjected controls (left). FIG. 1N-B provides DUX4 misexpression results in abnormal eye pigmentation (left), asymmetric fin development (middle), and altered ear morphology (right). FIG. 1N-C illustrates mosaic expression of DUX4 (left, purple nuclei) in a stable transgenic model at day 4 postfertilization. Aging of these transgenic fish results in muscle degeneration and fat infiltration (right) compared to no DUX4 control fish (middle) by 2 weeks.

FIG. 2A is a schematic of gene knockout and activation using Cas9. Gene knock-out is achieved by Cas9-induced cleavage and indel formation at target genomic sites complementary to the sgRNA sequence. FIG. 2B illustrates gene activation achieved by inactivated Cas9 and fusion of activation domains (VP64, p65, HSF1) to recruit transcriptional machinery to transcriptional start sites complementary to the sgRNA sequence.

FIG. 3A shows HEK293T cells transduced with the CRISPR loss-of-function library (top left).

FIG. 3B depicts gene-edited cells transduced with DUX4 baculovirus and widespread cell death occurs within 48 hrs.

FIG. 3C shows that cells survive if they harbor gene knock-out confers resistance to DUX4 toxicity.

FIG. 3D shows that DUX4 'resistant' cells proliferate as colonies (bottom right).

FIG. 4A shows baseline raw read counts before DUX4 selection. A mean library distribution of 300× across all 120,000 sgRNA constructs.

FIG. 4B shows individual sgRNA representation before and after DUX4 selection shows enrichment of specific sgRNAs.

FIG. 4C shows normalized read counts of 6 sgRNAs for two significant candidate genes before and after DUX4 selection.

FIG. 6 provides 3 tables showing genes identified in loss-of-function CRISPR screens carried out in HEK293T cells for genes whose loss results in resistance to Dux4.

FIG. 7 provides 2 tables showing genes identified in loss-of-function CRISPR screens carried out in MB135 immortalized human myoblasts for genes whose loss results in resistance to Dux4.

FIGS. 8A and 8B includes four micrographs of different cell types: HEK293T vs immortalized human myoblast and different methods of DUX4 expression. FIG. 8A is a micrograph of the cell types following DUX4 expression via baculovirus, and FIG. 8B is a micrograph of the cell lines following expression of DUX4 from adoxycyline (dox)-inducible transgene.

FIG. 14A is a schematic diagram showing a method for assaying cell death by measuring Caspase 3/7 activity using a luciferase read-out.

FIG. 14B presents graphical data generated from the doxycycline-inducible assay.

FIG. 17A includes a series of micrographs. Fluorescence from labeled caspase is visible (fluorescein isothiocynate (FITC)) in a DUX4 inducible cell line after 48 hours of doxy cy cline treatment.

FIG. 17B provides images of single gene knock-outs with reduced capase flurescence after 48 hours of doxy cy cline treatment.

FIG. 17C presents a histogram of the quantified data from the images presented in FIGS. 17A and 17B.

FIG. 17D provides images indicating that drug compounds (i.e., rapamycin, Ly294002, wortmannin, and herbimycin) reduced caspase fluorescence after 48 hours of doxycydine treatment, and FIG. 17E presents a histogram summarizing the quantified data from these images.

DETAILED DESCRIPTION OF THE INVENTION

The invention features compositions and methods that are useful for the treatment of FSHD.

Facioscapulohumeral dystrophy (FSHD) is a unique and complex autosomal dominant muscular dystrophy with an incomplete genetic picture. FSHD is linked to a truncated repetitive region (DZ4 repeat) in the subtelomeric region of chromosome 4. Within each DZ4 repeat is a DUX4 open reading frame (FIG. 1A-1H). The likely mechanism of disease is linked to epigenetic changes at the 4q35 locus, causing misexpression of the retro-transposon derived gene, DUX4. Levels of DUX4 expression vary between patients. Interestingly, in affected patients only approximately 1 in every 200-1000 myonuclei shows DUX4 expression (FIG. 1I). Transient bursts results in high levels of DUX4 expression in the rare nuclei, which can spread to adjacent nuclei along a single myotube. The expression of DUX4 is toxic to cells in vivo and in vitro (FIG. 1K, 1L).

The DUX4 gene encodes a transcription factor whose expression is rare, but extremely toxic. DUX4 transcription factor controls more than 100 early developmental genes. Misexpression of DUX4 is hypothesized to induce inappropriate expression of downstream genes to cause disease pathogenesis. How DUX4 and its target genes cause disease remain unknown, but clinical evidence suggests that DUX4 misexpression is not an exclusive determinant of FSHD. Non-manifesting carriers of FSHD alleles who are found to express DUX4, point to the existence of genetic modifiers that may act to suppress DUX4 toxicity. The clinical, histopathological and molecular evidence for asymptomatic/non-manifesting carriers of FSHD is provided at FIGS. 1A-1F. As reported herein below, a genome-wide CRISPR loss-of-function library was used to identify genes that modulate DUX4 induced toxicity and act as genetic modifiers of FSHD (FIG. 1M). This powerful resource has enabled the assessment of the impact of all loss-of-function gene edits across the entire genome. This approach permitted the isolation of genes that influence survivability of DUX4 toxicity. These genes were validated in vitro by generation of individual knock-out lines, using a Caspase-3/7 assay to quantify reduced DUX4-induced apoptosis, and using inhibitor compounds to mimic gene knock-outs. These genes are also being evaluated in vivo.

CRISPR Screening

Figure 2A:
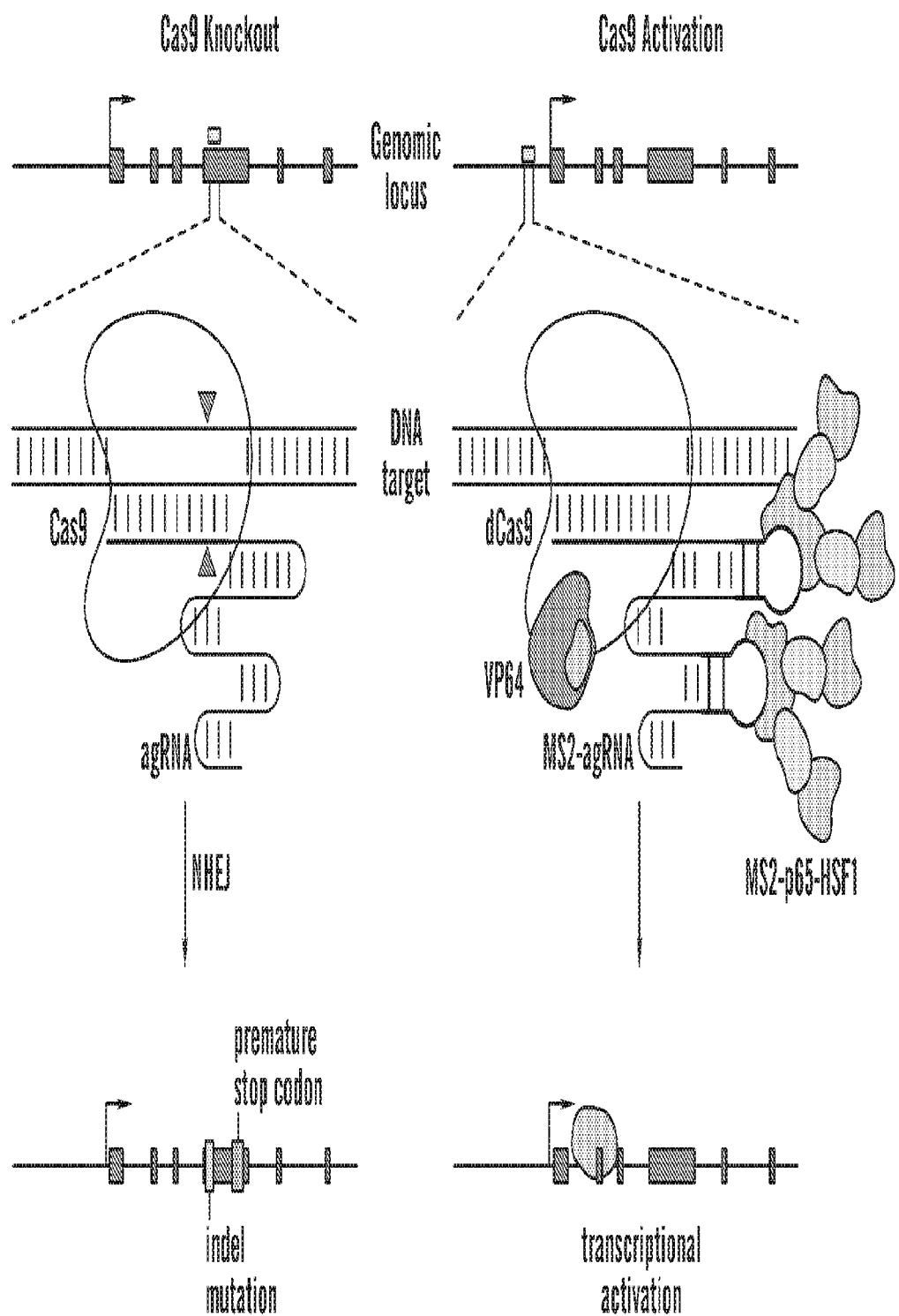
FIGS. 2A and 2B are schematic diagrams showing approaches to gene knock-out and activation in forward genetic screens.
Figure 2A:
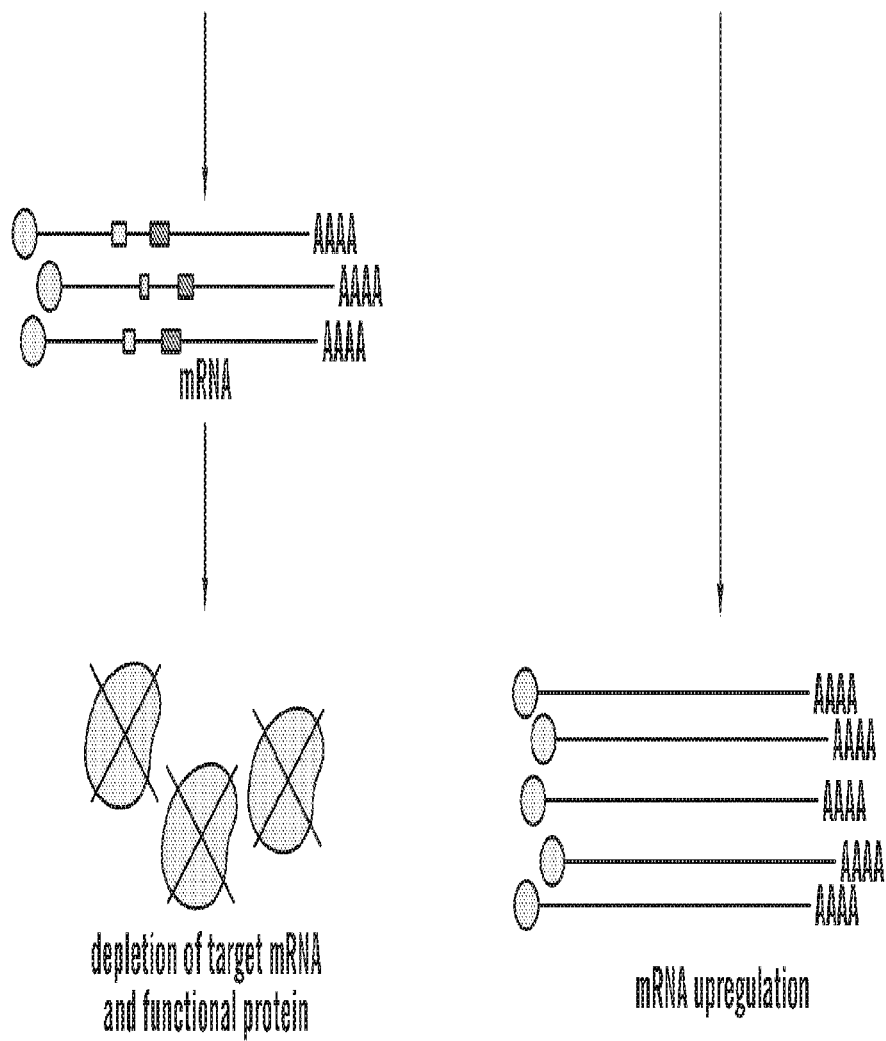
Figure 2B:
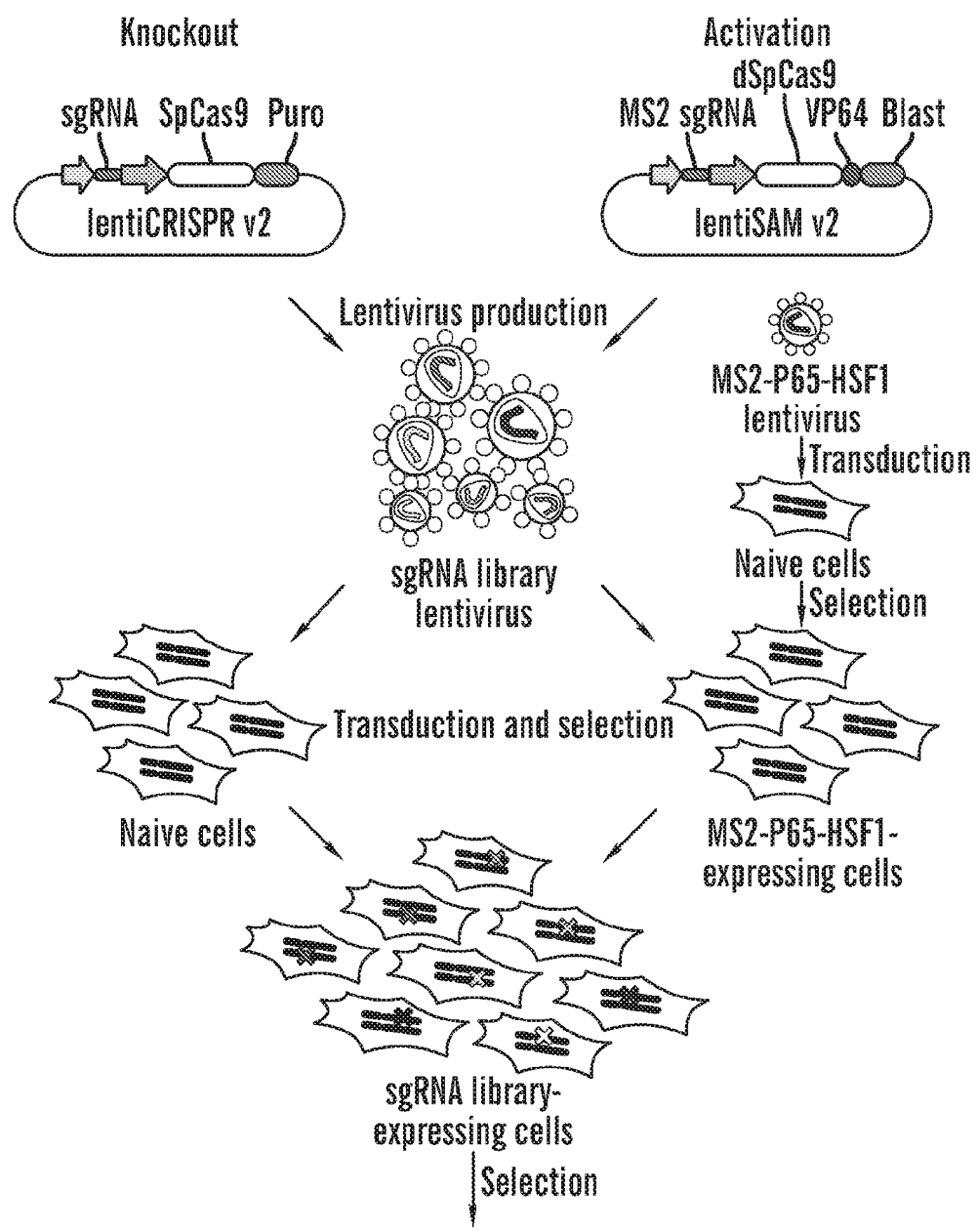
Figure 2B:
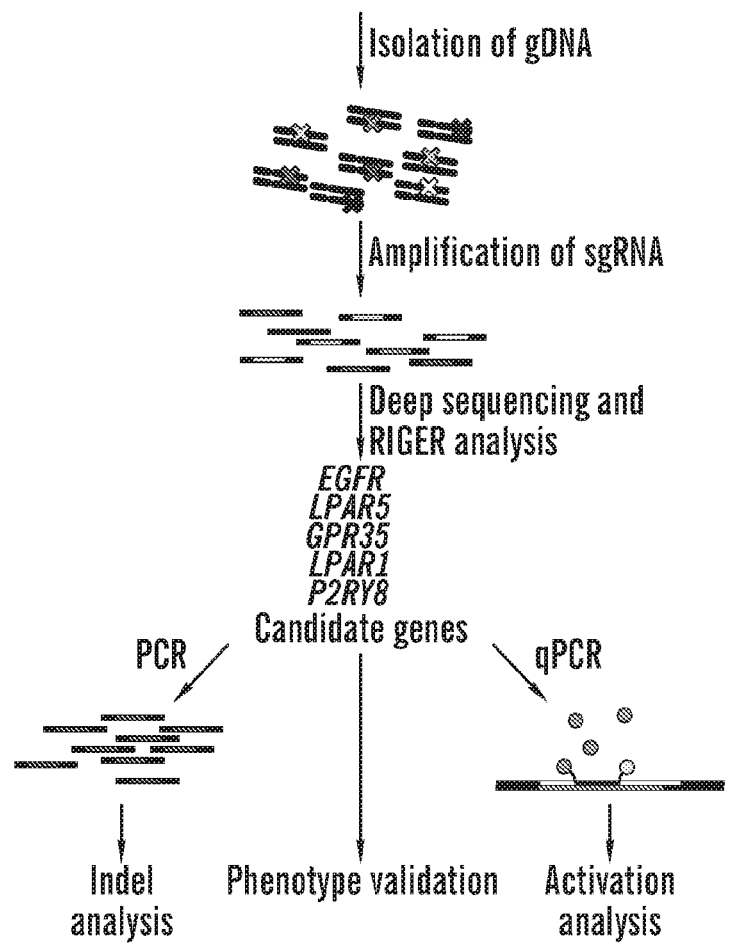
Figure 2C:
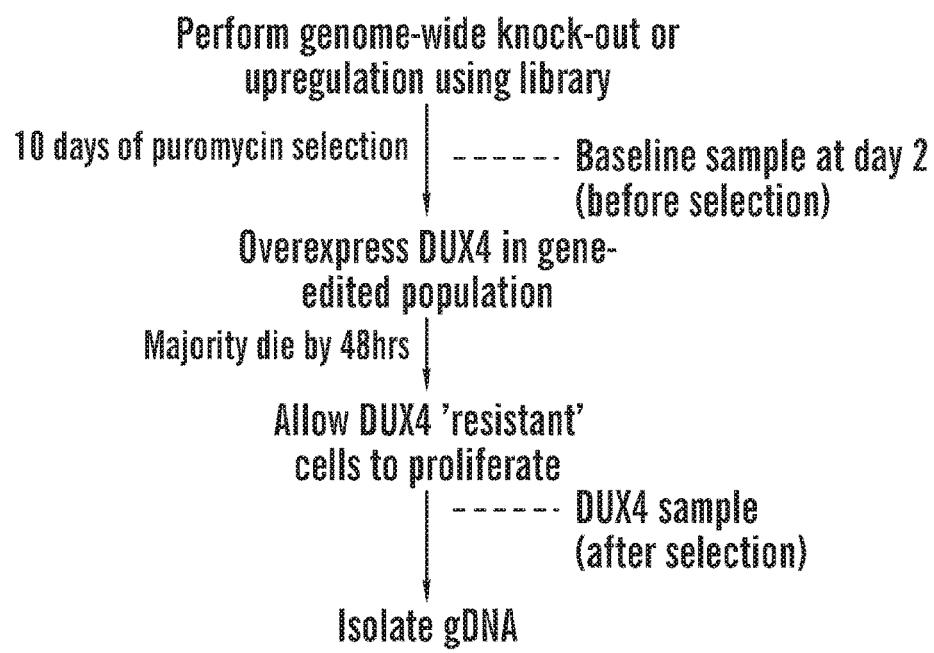
FIG. 2C shows a screening strategy for genome-wide CRISPR loss and gain-of-function screens.

The emergence of CRISPR gene editing technology has enabled the systematic interrogation of gene function on a genome-wide scale (Shalem et al. Science (New York, N.Y.) 343 (6166): 84-87 2014). Loss- or gain-of-function perturbations across the entire genome have recently been made possible by way of incorporating Cas9 endonuclease from the microbial immune system CRISPR (clustered regularly interspaced short palindromic repeats) with single guide RNA (sgRNA) libraries to induce precise DNA modification at targeted sites [(Cong et al. 2013). When combined with efficient lentiviral delivery, genome-scale CRISPR-Cas9 editing platforms provide a powerful strategy to perform loss- and gain-of-function (LoF and GoF, respectively) screens to elucidate gene function (Miles, Garippa, and Poirier, FEBS 283: 3170-80 2016). In LoF screens, Cas9 is employed to generate a double-stranded break at a precise target locus, triggering an error-prone repair mechanism that introduces frameshift indels and ultimately leads to loss-of-function mutations (FIG. 2A). The use of CRISPR LoF libraries has thus far been used to determine essential genes involved in drug resistance (Shalem et al. 2014, supra) and cancer metastasis (Chen et al. Cell 160 (6) Elsevier Inc.: 1246-60 2015). The LoF Gecko library utilized in our loss-of-function DUX4 resistance screen consisted of 123, 411 sgRNAs to target 19,050 coding genes (6 different guides per gene). GoF screens in comparison are more complex, requiring several engineered components such as a fusion complex involving an inactivated Cas9 and a transcriptional activator (Cas9-VP64); and modified sgRNAs that incorporate MS2 bacteriophage coat proteins, enabling it to recruit two other activation domains (p65 and HSF-1) to the Cas9-VP64 complex (FIG. 2B) (Konermann et al. 2014). Thus the Synergistic activation mediator (SAM) complex utilizes three different transcriptional effectors to achieve transcriptional up-regulation. The SAM library proposed for use in our GoF DUX4 screen includes 70,290 unique sgRNAs designed to up-regulate expression of 23,430 coding genes (3 different guides per gene). These sgRNA target sites are spread across the proximal promoter and the transcriptional start site of each gene, and have been demonstrated to up-regulate gene expression anywhere between two- to fifteen-fold. Both LoF and GoF plasmid libraries are commercially available through Addgene. Pooled libraries must be packaged into lentivirus particles and titered such that most cells are transduced with only one stably integrating sgRNA. Screening strategy is outlined in FIG. 2C.

Significant CRISPR hits (FIGS. 2D and 2E) can be mined for additional drug targets. We disclose herein a platform for therapeutic discovery and testing of drug compounds that target DUX4-induced toxicity in cells and a whole-animal model (FIG. 2F).

FSHD Zebrafish Model

FSHD has proven to be a difficult disease to model in animals given the primate-specific origins of DUX4, its sporadic activation and mosaic expression, as well as the complex epigenetic components associated with the disease.

Figure 1A:
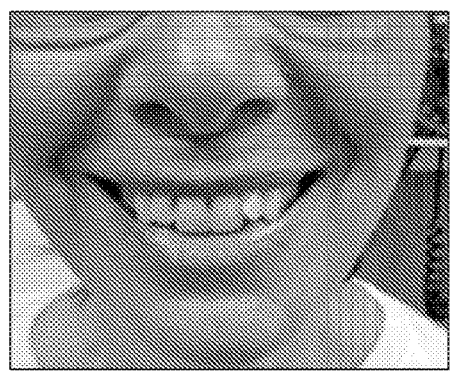
Figure 1B:
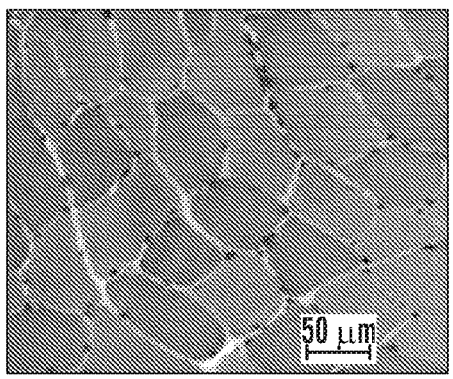
FIG. 1B is a micrograph showing a normal H&E bicep histology (B) and normal MRI of thighs in (FIG. 1C) and (FIG. 1D).
Figure 1C:
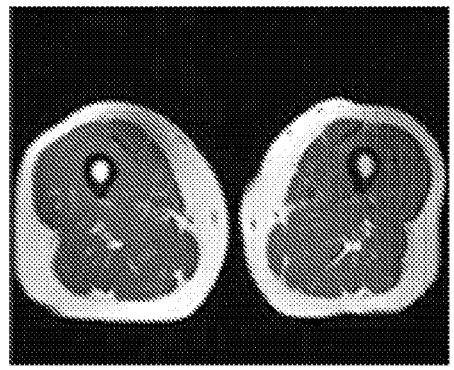
Figure 1D:
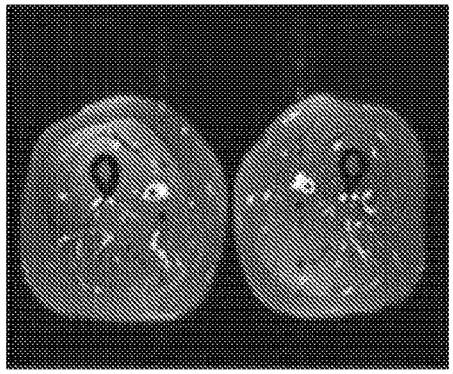
Figure 1E:
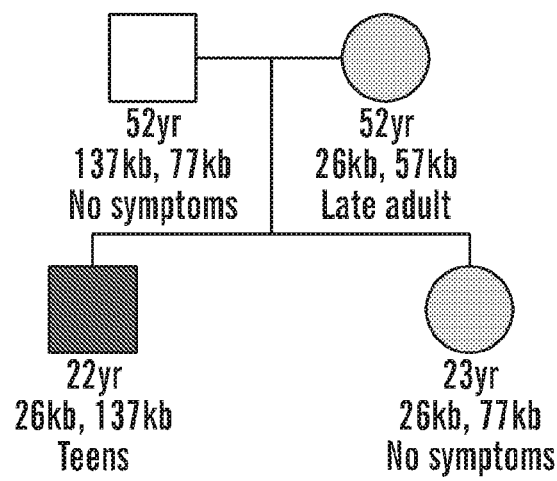
FIG. 1E shows a family tree of an FSHD family from Dr. Kathryn Wagner's Wellstone cohort (affected individuals will harbor at least one truncated D4Z4 allele of less than 35 kb). Two siblings inherit a truncated D4Z4 allele of 26 kb from their affected mother; one develops clinical symptoms during teenage years, while the other continues to remain asymptomatic.
Figure 1F:
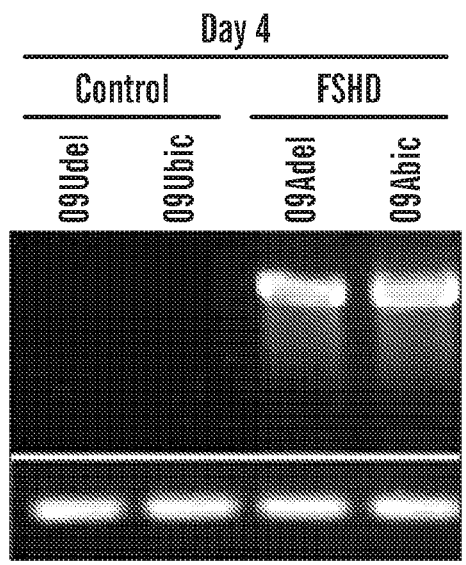
FIG. 1F is an image showing (left panel) RT-PCR expression of DUX4 transcript in affected patient's deltoid (09Adel) and bicep muscle (09Abic), but absent in their first-degree relative's deltoid (09Udel) and bicep (09Ubic) muscle.
Figure 1G:
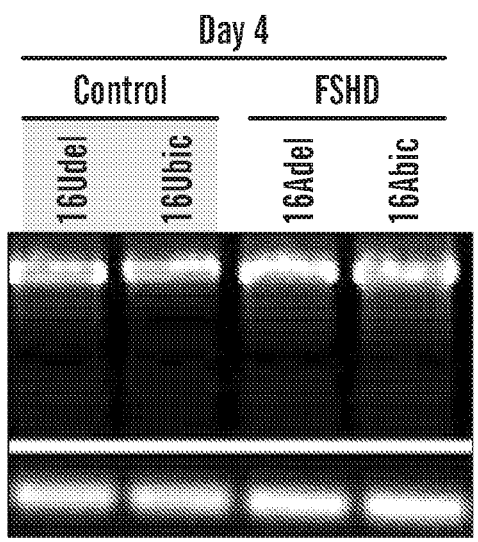
FIG. 1G is an image showing evidence of DUX4 transcript expression in patient 16A (bicep and deltoid), which is also detected in their first-degree relative (16U bicep and deltoid samples) who harbor no clinical symptoms.
Figure 1I:
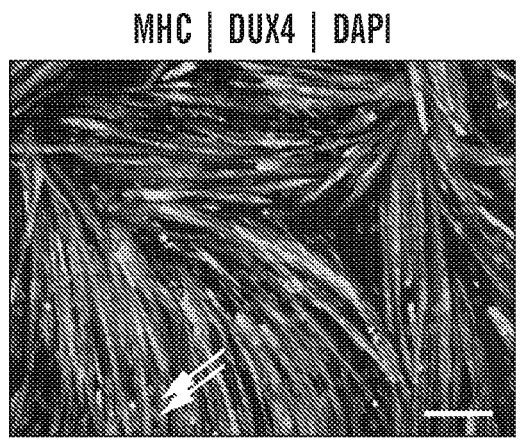
FIG. 1I a micrograph showing that transcriptional activation of DUX4 is sporadic and rare. Once activated in rare nuclei, expression spreads to neighboring nuclei within a myotube.
Figure 1J:
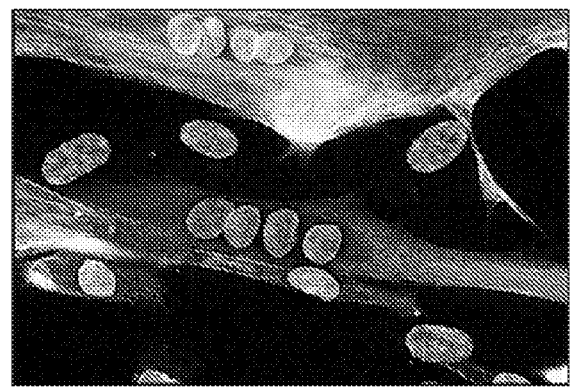
FIG. 1J is a micrograph of cultured FSHD skeletal muscle with a rare burst of DUX4 protein expression in the nucleus of a myofiber.
Figure 1K:
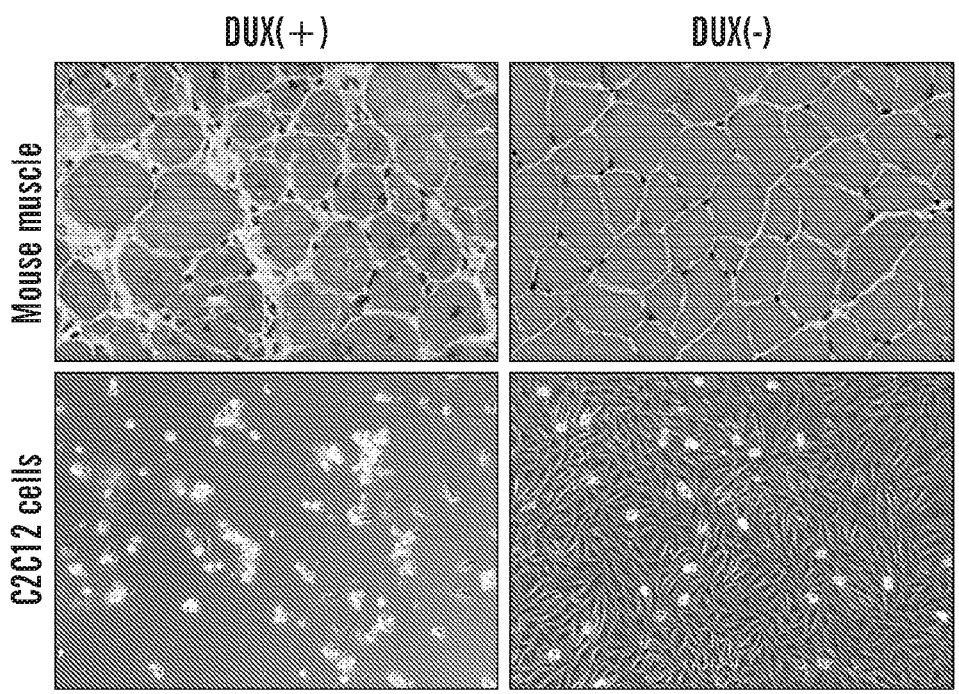
FIG. 1K includes four micrographs that show the toxic effect of DUX4 expression in cells and muscle fibers.
Figure 1L:
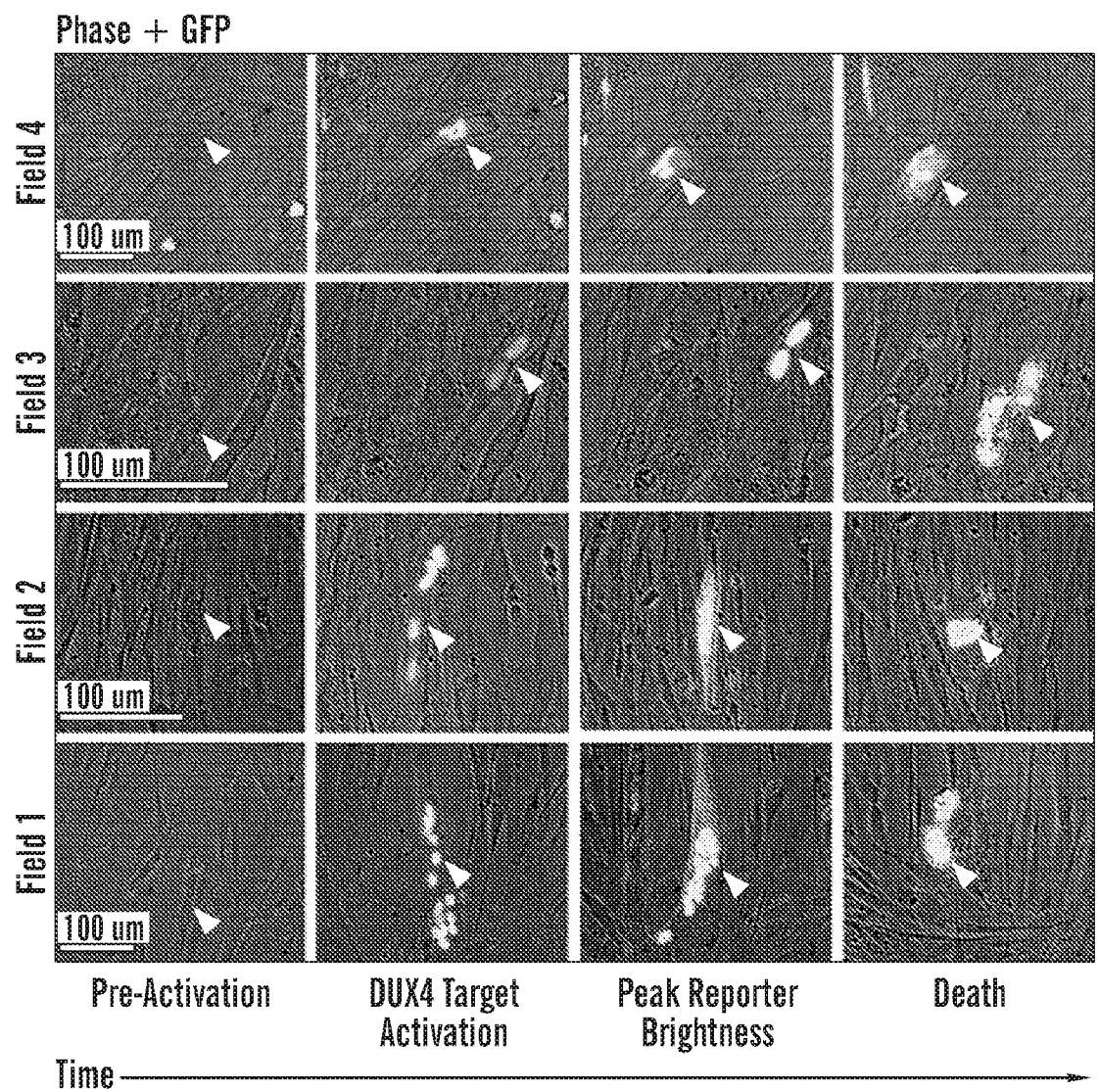
FIG. 1L includes a series of micrographs showing that an endogenous burst of DUX4 expression leads to cell death in FSHD cells (Rickard 2015 HMG).
Figure 1M:
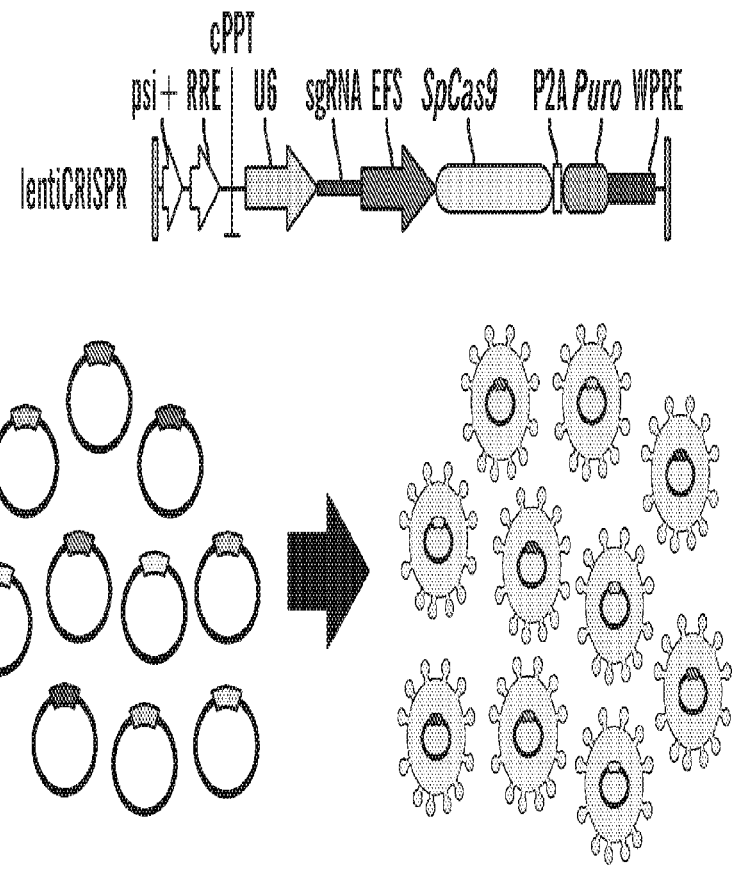
FIG. 1M is a schematic showing a commercially available library of CRISPR constructs that target all human genes.

Our published DUX4 zebrafish model was the first to recapitulate the muscle-eye-ear combination of phenotypes described in human FSHD (FIGS. 1N-A, 1N-B, 1N-C). This was achieved by injection of very low levels of DUX4 (1 RNA molecule per 1000 cells) during zebrafish development, which resulted in muscle degeneration (FIG. 1N-A, right panel), and asymmetric abnormalities of the eyes and ears (FIG. 1N-B), consistent with affected regions in human FSHD. In addition, we have developed a more stable DUX4 inducible transgenic model that mimics the low mosaic expression of DUX4 in human skeletal muscle, and shows evidence of muscle degeneration by 2 weeks (FIG. 1N-C). These established DUX4 models of FSHD provide for functional follow-up experiments for candidate genes identified in CRISPR screens.

To achieve candidate gene upregulation in the DUX4 zebrafish model, we will PCR amplify and clone our candidate genes into an expression vector suitable for in vitro transcription, similar to methods used for DUX4 overexpression (Mitsuhashi et al. *Human Molecular Genetics* 22 (3): 568-77 (2013)). Synthesized mRNA for each candidate gene will be microinjected into fertilized zebrafish eggs at the one-cell stage to induce candidate gene upregulation. Quantitative PCR will be used to verify gene upregulation within the first few days of gestation. Once upregulation is established, we will simultaneously inject mRNA of our candidate gene and DUX4, to look for rescue of DUX4-induced phenotypes. Candidate genes are considered validated if they are able to ameliorate DUX4-induced phenotypes that develop by day 4 post-fertilization such as deformities of the skeletal muscle, fins, and eyes. The injection model is a high-throughput approach where potentially hundreds of fish injections can be subject to expression analysis and assessment of phenotype to obtain statistical significance.

Inhibitory Nucleic Acids

Inhibitory nucleic acid molecules are those oligonucleotides that inhibit the expression or activity of a polypeptide that functions in a hypoxia response pathway (e.g., Hif1alpha, ARNT/HIF1beta, CDKN1A, p21, CREBBP, CBP, and ZCCHC14). Such oligonucleotides include single and double stranded nucleic acid molecules (e.g., DNA, RNA, and analogs thereof) that bind a nucleic acid molecule that encodes a polypeptide that that functions in a hypoxia response pathway (e.g., antisense molecules, siRNA, shRNA) as well as nucleic acid molecules that bind directly to the polypeptide to modulate its biological activity (e.g., aptamers). In one embodiment, the inhibitory nucleic acid molecule inhibits the expression of Hif1 alpha.

siRNA

Short twenty-one to twenty-five nucleotide double-stranded RNAs are effective at down-regulating gene expression (Zamore et al., Cell 101: 25-33; Elbashir et al., Nature 411: 494-498, 2001, hereby incorporated by reference). The therapeutic effectiveness of an sirNA approach in mammals was demonstrated in vivo by McCaffrey et al. (Nature 418: 38-39.2002).

Given the sequence of a target gene, siRNAs may be designed to inactivate that gene. Such siRNAs, for example, could be administered directly to an affected tissue, or administered systemically. The nucleic acid sequence of a gene can be used to design small interfering RNAs (siRNAs). The 21 to 25 nucleotide siRNAs may be used, for example, as therapeutics to treat FSHD.

The inhibitory nucleic acid molecules of the present invention may be employed as double-stranded RNAs for RNA interference (RNAi)-mediated knock-down of expression. In one embodiment, expression of a gene listed in Table 2 or 3 is reduced in a skeletal muscle cell. RNAi is a method for decreasing the cellular expression of specific proteins of interest (reviewed in Tuschl, Chembiochem 2:239-245, 2001; Sharp, Genes & Devel. 15:485-490, 2000; Hutvagner and Zamore, Curr. Opin. Genet. Devel. 12:225-232, 2002; and Hannon, Nature 418:244-251, 2002). The introduction of siRNAs into cells either by transfection of dsRNAs or through expression of siRNAs using a plasmid-based expression system is increasingly being used to create loss-of-function phenotypes in mammalian cells.

In one embodiment of the invention, a double-stranded RNA (dsRNA) molecule is made that includes between eight and nineteen consecutive nucleobases of a nucleobase oligomer of the invention. The dsRNA can be two distinct strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Genes & Devel. 16:948-958, 2002. Paul et al. Nature Biotechnol. 20:505-508, 2002; Sui et al. Proc. Natl. Acad. Sci. USA 99:5515-5520, 2002; Yu et al. Proc. Natl. Acad. Sci. USA 99:6047-6052, 2002; Miyagishi et al. Nature Biotechnol. 20:497-500, 2002; and Lee et al. Nature Biotechnol. 20:500-505 2002, each of which is hereby incorporated by reference.

Small hairpin RNAs (shRNAs) comprise an RNA sequence having a stem-loop structure. A "stem-loop structure" refers to a nucleic acid having a secondary structure that includes a region of nucleotides which are known or predicted to form a double strand or duplex (stem portion) that is linked on one side by a region of predominantly single-stranded nucleotides (loop portion). The term "hairpin" is also used herein to refer to stem-loop structures. Such structures are well known in the art and the term is used consistently with its known meaning in the art. As is known in the art, the secondary structure does not require exact base-pairing. Thus, the stem can include one or more base mismatches or bulges. Alternatively, the base-pairing can be exact, i.e. not include any mismatches. The multiple stem-loop structures can be linked to one another through a linker, such as, for example, a nucleic acid linker, a miRNA flanking sequence, other molecule, or some combination thereof.

As used herein, the term "small hairpin RNA" includes a conventional stem-loop shRNA, which forms a precursor miRNA (pre-miRNA). While there may be some variation in range, a conventional stem-loop shRNA can comprise a stem ranging from 19 to 29 bp, and a loop ranging from 4 to 30 bp. "shRNA" also includes micro-RNA embedded shRNAs (miRNA-based shRNAs), wherein the guide strand and the passenger strand of the miRNA duplex are incorporated into an existing (or natural) miRNA or into a modified or synthetic (designed) miRNA. In some instances, the precursor miRNA molecule can include more than one stem-loop structure. MicroRNAs are endogenously encoded RNA molecules that are about 22-nucleotides long and generally expressed in a highly tissue- or developmental-stage-specific fashion and that post-transcriptionally regulate target genes. More than 200 distinct miRNAs have been identified in plants and animals. These small regulatory RNAs are believed to serve important biological functions by two prevailing modes of action: (1) by repressing the translation of target mRNAs, and (2) through RNA interference (RNAi), that is, cleavage and degradation of mRNAs. In the latter case, miRNAs function analogously to small interfering RNAs (siRNAs). Thus, one can design and express artificial miRNAs based on the features of existing miRNA genes.

shRNAs can be expressed from DNA vectors to provide sustained silencing and high yield delivery into almost any cell type. In some embodiments, the vector is a viral vector. Exemplary viral vectors include retroviral, including lentiviral, adenoviral, baculoviral and avian viral vectors, and including such vectors allowing for stable, single-copy genomic integrations. Retroviruses from which the retroviral plasmid vectors can be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus. A retroviral plasmid vector can be employed to transduce packaging cell lines to form producer cell lines. Examples of packaging cells which can be transfected include, but are not limited to, the PE501, PA317, R-2, R-AM, PA12, T19-14x, VT-19-17-H2, RCRE, RCRIP, GP+E-86, GP+envAm12, and DAN cell lines as described in Miller, Human Gene Therapy 1:5-14 (1990), which is incorporated herein by reference in its entirety. The vector can transduce the packaging cells through any means known in the art. A producer cell line generates infectious retroviral vector particles which include polynucleotide encoding a DNA replication protein. Such retroviral vector particles then can be employed, to transduce eukaryotic cells, either in vitro or in vivo. The transduced eukaryotic cells will express a DNA replication protein.

Catalytic RNA molecules or ribozymes that include an antisense sequence of the present invention can be used to inhibit expression of a nucleic acid molecule in vivo (e.g., a nucleic acid molecule listed in Table 2 or 3). The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference.

Accordingly, the invention also features a catalytic RNA molecule that includes, in the binding arm, an antisense RNA having between eight and nineteen consecutive nucleobases. In preferred embodiments of this invention, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

Essentially any method for introducing a nucleic acid construct into cells can be employed. Physical methods of introducing nucleic acids include injection of a solution containing the construct, bombardment by particles covered by the construct, soaking a cell, tissue sample or organism in a solution of the nucleic acid, or electroporation of cell membranes in the presence of the construct. A viral construct packaged into a viral particle can be used to accomplish both efficient introduction of an expression construct into the cell and transcription of the encoded shRNA. Other methods known in the art for introducing nucleic acids to cells can be used, such as lipid-mediated carrier transport, chemical mediated transport, such as calcium phosphate, and the like. Thus the shRNA-encoding nucleic acid construct can be introduced along with components that perform one or more of the following activities: enhance RNA uptake by the cell, promote annealing of the duplex strands, stabilize the annealed strands, or otherwise increase inhibition of the target gene.

For expression within cells, DNA vectors, for example plasmid vectors comprising either an RNA polymerase II or RNA polymerase III promoter can be employed. Expression of endogenous miRNAs is controlled by RNA polymerase II (Pol II) promoters and in some cases, shRNAs are most efficiently driven by Pol II promoters, as compared to RNA polymerase III promoters (Dickins et al., 2005, Nat. Genet. 39: 914-921). In some embodiments, expression of the shRNA can be controlled by an inducible promoter or a conditional expression system, including, without limitation, RNA polymerase type II promoters. Examples of useful promoters in the context of the invention are tetracycline-inducible promoters (including TRE-tight), IPTG-inducible promoters, tetracycline transactivator systems, and reverse tetracycline transactivator (rtTA) systems. Constitutive promoters can also be used, as can cell- or tissue-specific promoters. Many promoters will be ubiquitous, such that they are expressed in all cell and tissue types. A certain embodiment uses tetracycline-responsive promoters, one of the most effective conditional gene expression systems in in vitro and in vivo studies. See International Patent Application PCT/US2003/030901 (Publication No. WO 2004-029219 A2) and Fewell et al., 2006, Drug Discovery Today 11: 975-982, for a description of inducible shRNA.

Delivery of Polynucleotides

Naked polynucleotides, or analogs thereof, are capable of entering mammalian cells and inhibiting expression of a gene of interest. Nonetheless, it may be desirable to utilize a formulation that aids in the delivery of oligonucleotides or other nucleobase oligomers to cells (see, e.g., U.S. Pat. Nos. 5,656,611, 5,753,613, 5,785,992, 6,120,798, 6,221,959, 6,346,613, and 6,353,055, each of which is hereby incorporated by reference).

Treatment with Agents that Inhibit a Hypoxia Response Pathway

The invention provides methods for the treatment of FSHD. Such methods involve the administration of agents that modulate a hypoxia response pathway. In one embodiment, the agent is an agent that inhibits the expression or activity of Hif1alpha, ARNT/HIF1beta, CDKN1A, p21, CREBBP, CBP, and ZCCHC14.

Therapy may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the kind of cancer being treated, the age and condition of the patient, the stage and type of the patient's disease, and how the patient's body responds to the treatment. Drug administration may be performed at different intervals (e.g., daily, weekly, or monthly).

Oligonucleotides and Other Nucleobase Oligomers

At least two types of oligonucleotides induce the cleavage of RNA by RNase H: polydeoxynucleotides with phosphodiester (PO) or phosphorothioate (PS) linkages. Although 2'-OMe-RNA sequences exhibit a high affinity for RNA targets, these sequences are not substrates for RNase H. A desirable oligonucleotide is one based on 2'-modified oligonucleotides containing oligodeoxynucleotide gaps with some or all internucleotide linkages modified to phosphorothioates for nuclease resistance. The presence of methylphosphonate modifications increases the affinity of the oligonucleotide for its target RNA and thus reduces the $IC_{50}$. This modification also increases the nuclease resistance of the modified oligonucleotide. It is understood that the methods and reagents of the present invention may be used in conjunction with any technologies that may be developed, including covalently-closed multiple antisense (CMAS) oligonucleotides (Moon et al., Biochem J. 346:295-303, 2000; PCT Publication No. WO 00/61595), ribbon-type antisense (RiAS) oligonucleotides (Moon et al., J. Biol. Chem. 275: 4647-4653, 2000; PCT Publication No. WO 00/61595), and large circular antisense oligonucleotides (U.S. Patent Application Publication No. US 2002/0168631 A1).

As is known in the art, a nucleoside is a nucleobase-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure; open linear structures are generally preferred. Within the oligonucleotide structure, the phosphate groups are commonly referred to as forming the backbone of the oligonucleotide. The normal linkage or backbone of RNA and DNA is a 3' to 5' phosphodiester linkage.

Specific examples of preferred nucleobase oligomers useful in this invention include oligonucleotides containing modified backbones or non-natural internucleoside linkages. As defined in this specification, nucleobase oligomers having modified backbones include those that retain a phosphorus atom in the backbone and those that do not have a phosphorus atom in the backbone. For the purposes of this specification, modified oligonucleotides that do not have a phosphorus atom in their internucleoside backbone are also considered to be nucleobase oligomers.

Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity, wherein the adjacent pairs of nucleoside units are linked 3'-5' to 5'-3' or 2'-5' to 5'-2'. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleobase oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH.sub.2 component parts. Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other nucleobase oligomers, both the sugar and the internucleoside linkage, i.e., the backbone, are replaced with novel groups. The nucleobase units are maintained for hybridization with a gene (e.g., Hif1 alpha, ARNT/HIF1beta, CDKN1A, p21, CREBBP, CBP, and ZCCHC14). One such nucleobase oligomer, is referred to as a Peptide Nucleic Acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Methods for making and using these nucleobase oligomers are described, for example, in "Peptide Nucleic Acids: Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In particular embodiments of the invention, the nucleobase oligomers have phosphorothioate backbones and nucleosides with heteroatom backbones, and in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$—, and —O—N($CH_3$)—$CH_2$—$CH_2$—. In other embodiments, the oligonucleotides have morpholino backbone structures described in U.S. Pat. No. 5,034,506.

Nucleobase oligomers may also contain one or more substituted sugar moieties. Nucleobase oligomers comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)nON[(CH_2)_nCH_3)]_2$, where n and m are from 1 to about 10. Other preferred nucleobase oligomers include one of the following at the 2' position: $C_1$ to $C_{10}$ lower alkyl, substituted lower alkyl, alkaryl, aralkyl, O-alkaryl, or O-aralkyl, SH, $SCH_3$, OCN, Cl, Br, CN, $CF_3$, $OCF_3$, $SOCH_3$, $SO_2CH_3$, $ONO_2$, $NO_2$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of a nucleobase oligomer, or a group for improving the pharmacodynamic properties of an nucleobase oligomer, and other substituents having similar properties. Preferred modifications are 2'-O-methyl and 2'-methoxyethoxy (2'-O—$CH_2CH_2OCH_3$, also known as 2'-O-(2-methoxyethyl) or 2'-MOE). Another desirable modification is 2'-dimethylaminooxyethoxy (i.e., $O(CH_2)_2ON(CH_3)_2$), also known as 2'-DMAOE. Other modifications include, 2'-aminopropoxy (2'-$OCH_2CH_2CH_2NH_2$) and 2'-fluoro (2'-F). Similar modifications may also be made at other positions on an oligonucleotide or other nucleobase oligomer, particularly the 3' position of the sugar on the 3' terminal nucleotide or in 2'-5' linked oligonucleotides and the 5' position of 5' terminal nucleotide. Nucleobase oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleobase oligomers may also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine; 2-propyl and other alkyl derivatives of adenine and guanine; 2-thiouracil, 2-thiothymine and 2-thiocytosine; 5-halouracil and cytosine; 5-propynyl uracil and cytosine; 6-azo uracil, cytosine and thymine; 5-uracil (pseudouracil); 4-thiouracil; 8-halo, 8-amino, 8-thiol, 8-thioalkyl, 8-hydroxyl and other 8-substituted adenines and guanines; 5-halo (e.g., 5-bromo), 5-trifluoromethyl and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of an antisense oligonucleotide of the invention. These include 5-substituted pyrimidines, 6-azapyrimidines, and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., eds., Antisense Research and Applications, CRC Press, Boca Raton, 1993, pp. 276-278) and are desirable base substitutions, even more particularly when combined with 2'-O-methoxyethyl or 2'-O-methyl sugar modifications. Representative United States patents that teach the preparation of certain of the above noted modified nucleobases as well as other modified nucleobases include U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,750,692, each of which is herein incorporated by reference.

Another modification of a nucleobase oligomer of the invention involves chemically linking to the nucleobase oligomer one or more moieties or conjugates that enhance the activity, cellular distribution, or cellular uptake of the oligonucleotide. Such moieties include but are not limited to lipid moieties such as a cholesterol moiety (Letsinger et al., Proc. Natl. Acad. Sci. USA, 86:6553-6556, 1989), cholic acid (Manoharan et al., Bioorg. Med. Chem. Let, 4:1053-1060, 1994), a thioether, e.g., hexyl-S-tritylthiol (Manoharan et al., Ann. N.Y. Acad. Sci., 660:306-309, 1992; Manoharan et al., Bioorg. Med. Chem. Let., 3:2765-2770, 1993), a thiocholesterol (Oberhauser et al., Nucl. Acids Res., 20:533-538: 1992), an aliphatic chain, e.g., dodecandiol or undecyl residues (Saison-Behmoaras et al., EMBO J., 10:1111-1118, 1991; Kabanov et al., FEBS Lett., 259:327-330, 1990; Svinarchuk et al., Biochimie, 75:49-54, 1993), a phospholipid, e.g., di-hexadecyl-rac-glycerol or triethylammonium 1,2-di-O-hexadecyl-rac-glycero-3-H-phosphonate (Manoharan et al., Tetrahedron Lett., 36:3651-3654, 1995; Shea et al., Nucl. Acids Res., 18:3777-3783, 1990), a polyamine or a polyethylene glycol chain (Manoharan et al., Nucleosides & Nucleotides, 14:969-973, 1995), or adamantane acetic acid (Manoharan et al., Tetrahedron Lett., 36:3651-3654, 1995), a palmityl moiety (Mishra et al., Biochim. Biophys. Acta, 1264:229-237, 1995), or an octadecylamine or hexylamino-carbonyl-oxycholesterol moiety (Crooke et al., J. Pharmacol. Exp. Ther., 277:923-937, 1996. Representative United States patents that teach the preparation of such nucleobase oligomer conjugates include U.S. Pat. Nos. 4,587,044; 4,605,735; 4,667,025; 4,762,779; 4,789,737; 4,824,941; 4,828,979; 4,835,263; 4,876,335; 4,904,582; 4,948,882; 4,958,013; 5,082,830; 5,109,124; 5,112,963; 5,118,802; 5,138,045; 5,214,136; 5,218,105; 5,245,022; 5,254,469; 5,258,506; 5,262,536; 5,272,250; 5,292,873; 5,317,098; 5,371,241, 5,391,723; 5,414,077; 5,416,203; 5,451,463; 5,486,603; 5,510,475; 5,512,439; 5,512,667; 5,514,785; 5,525,465; 5,541,313; 5,545,730; 5,552,538; 5,565,552; 5,567,810; 5,574,142; 5,578,717; 5,578,718; 5,580,731; 5,585,481; 5,587,371; 5,591,584; 5,595,726; 5,597,696; 5,599,923; 5,599,928; 5,608,046; and 5,688,941, each of which is herein incorporated by reference.

The present invention also includes nucleobase oligomers that are chimeric compounds. "Chimeric" nucleobase oligomers are nucleobase oligomers, particularly oligonucleotides, that contain two or more chemically distinct regions, each made up of at least one monomer unit, i.e., a nucleotide in the case of an oligonucleotide. These nucleobase oligomers typically contain at least one region where the nucleobase oligomer is modified to confer, upon the nucleobase oligomer, increased resistance to nuclease degradation, increased cellular uptake, and/or increased binding affinity for the target nucleic acid. An additional region of the nucleobase oligomer may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of nucleobase oligomer inhibition of gene expression. Consequently, comparable results can often be obtained with shorter nucleobase oligomers when chimeric nucleobase oligomers are used, compared to phosphorothioate deoxyoligonucleotides hybridizing to the same target region.

Chimeric nucleobase oligomers of the invention may be formed as composite structures of two or more nucleobase oligomers as described above. Such nucleobase oligomers, when oligonucleotides, have also been referred to in the art as hybrids or gapmers. Representative United States patents that teach the preparation of such hybrid structures include U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The nucleobase oligomers used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The nucleobase oligomers of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Therapeutic Methods

Agents identified as reducing the expression or activity of a member of a hypoxia response pathway (e.g., Hif1alpha, ARNT/HIF1beta, CDKN1A, p21, CREBBP, CBP, and ZCCHC14) are useful for preventing or ameliorating FSHD. In one therapeutic approach, an agent identified as described herein is administered to the site of a potential or actual disease-affected tissue or is administered systemically. The dosage of the administered agent depends on a number of factors, including the size and health of the individual patient. For any particular subject, the specific dosage regimes should be adjusted over time according to the individual need and the professional judgement of the person administering or supervising the administration of the compositions.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Genome-Wide CRISPR-Cas9 Loss-of-Function Screen

Figure 2D:
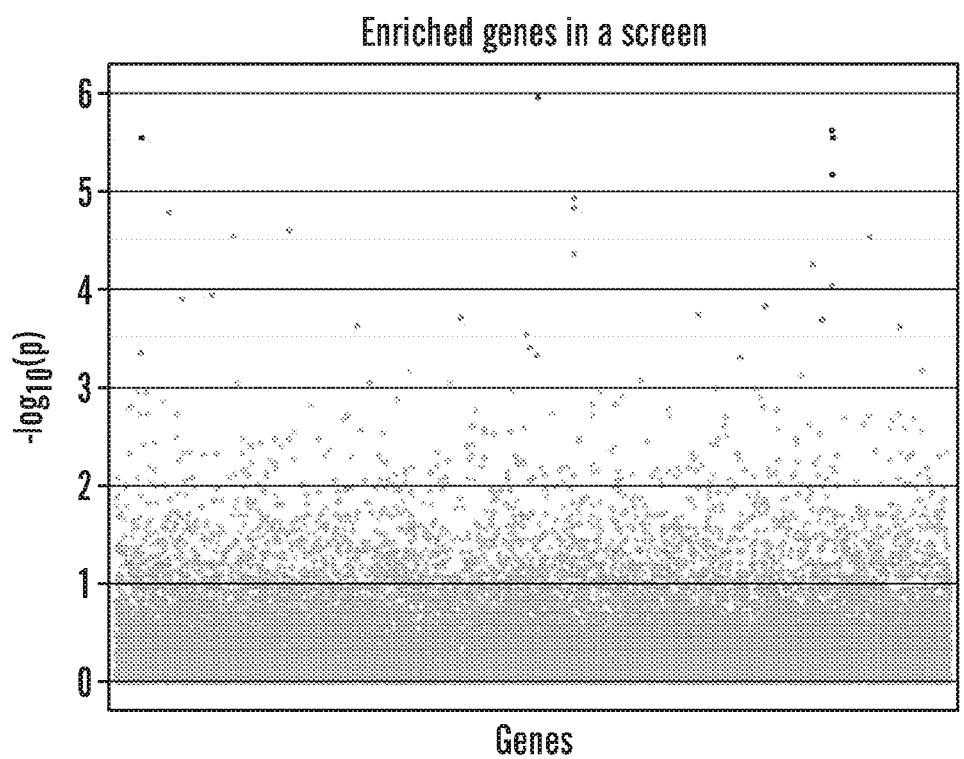
FIGS. 2D and 2E provide data related to the set of enriched genes (FIG. 2D) and those that were reproducibly identified (FIG. 2E).
Figure 2E:
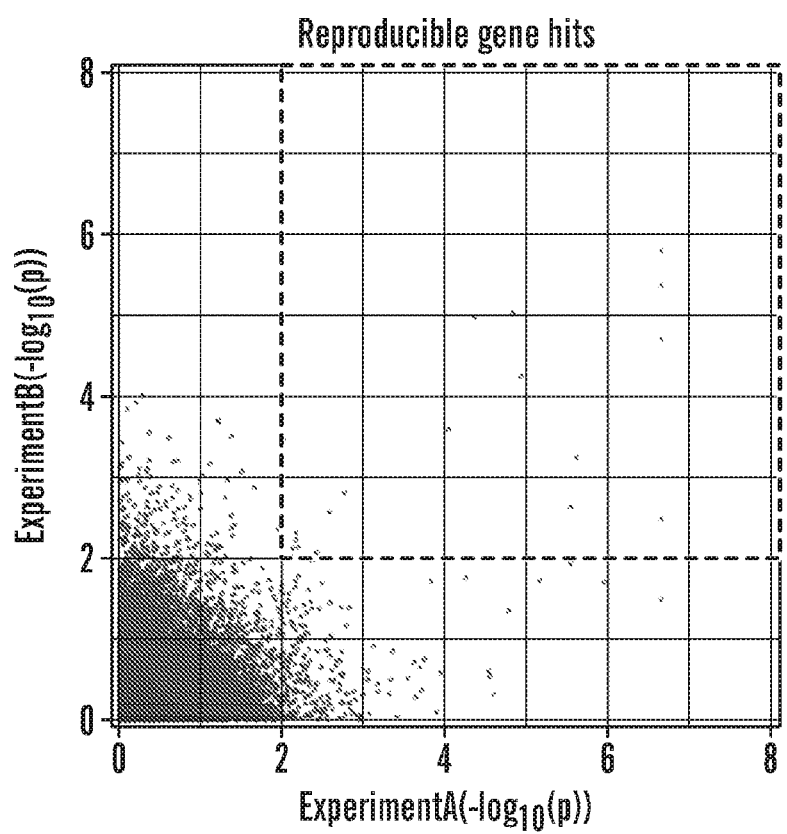
Figure 2F:
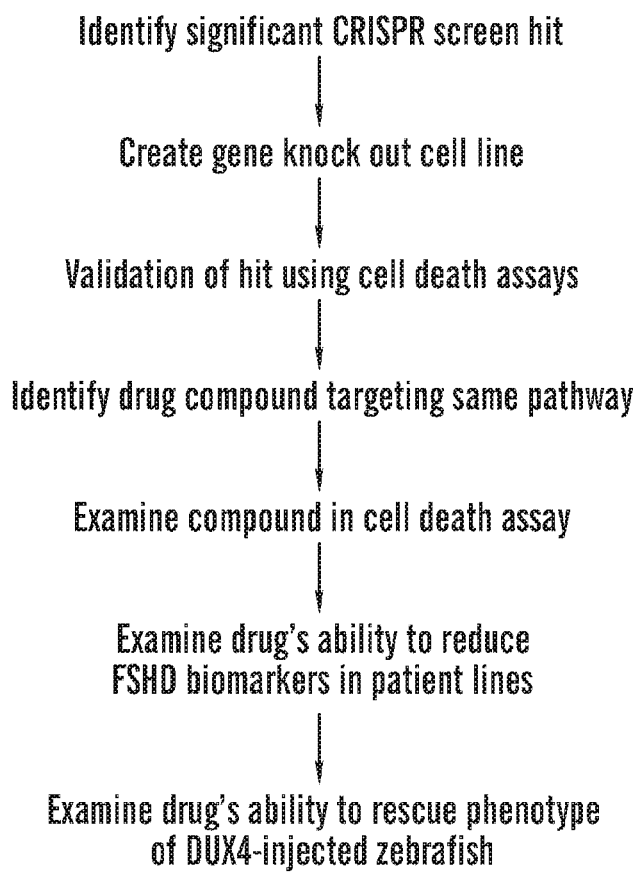
FIG. 2F provides a workflow for drug screening.

To date, we have successfully employed the CRISPR-Cas9 knock-out library to perform a genome-wide loss-of-function screen to identify genes whose knock-out confers resistance to DUX4 toxicity (FIGS. 2D, 2E). In these screens, DUX4 'resistant' cell populations were successfully isolated (FIGS. 3 and 4).

Figure 3A:
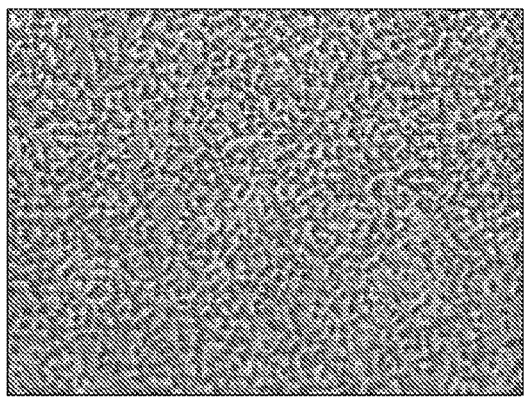
FIG. 3A-3D includes four micrographs showing results obtained in a genome-wide loss-of-function CRISPR screen to identify DUX4 resistant genes.
Figure 3B:
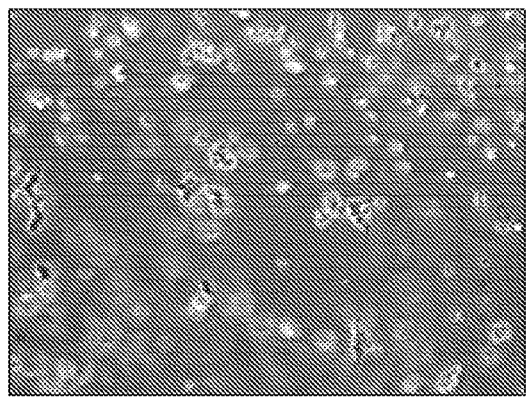
Figure 3C:
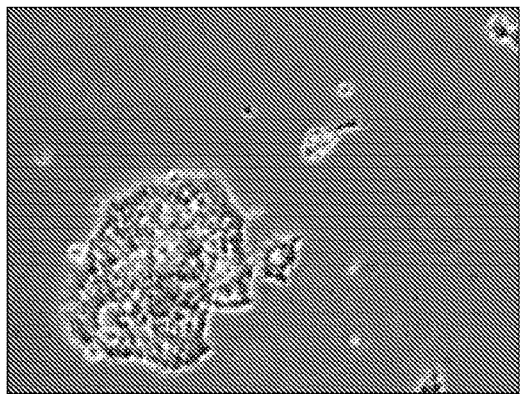
Figure 3D:
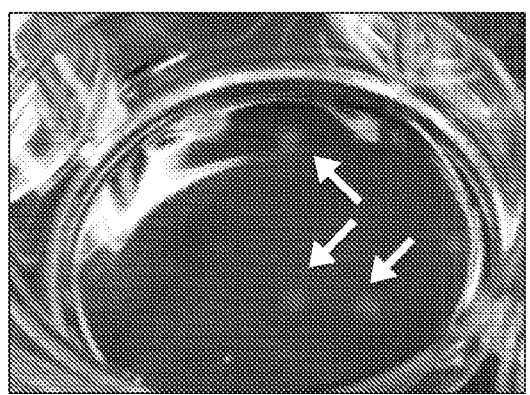
Figure 4A:
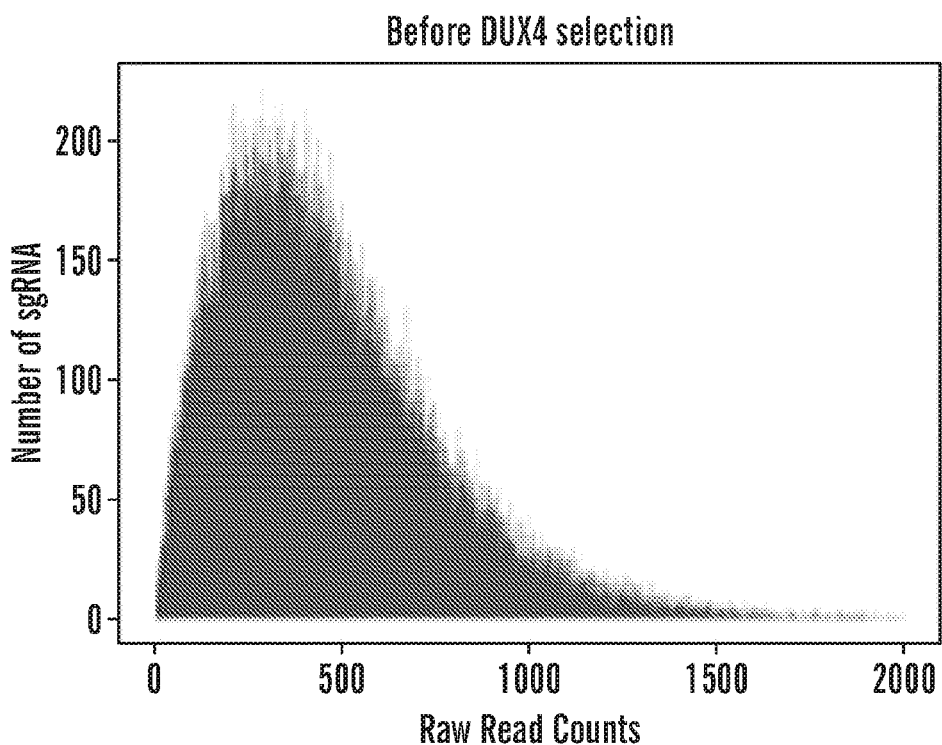
FIG. 4A-4C shows results of Next generation sequencing analysis of sgRNA.
Figure 4B:
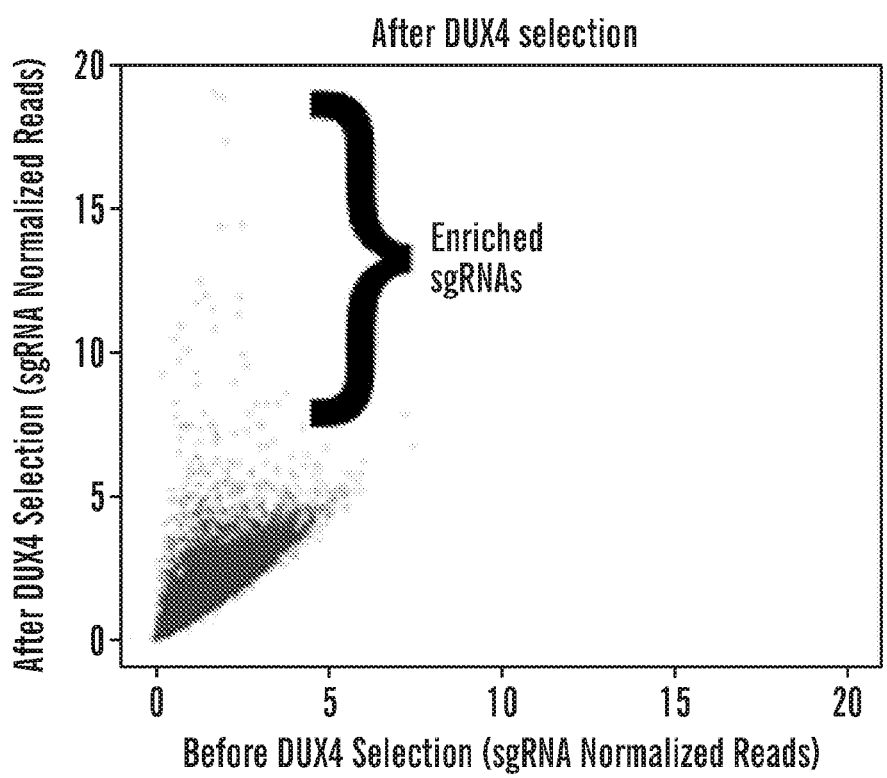
Figure 4C:
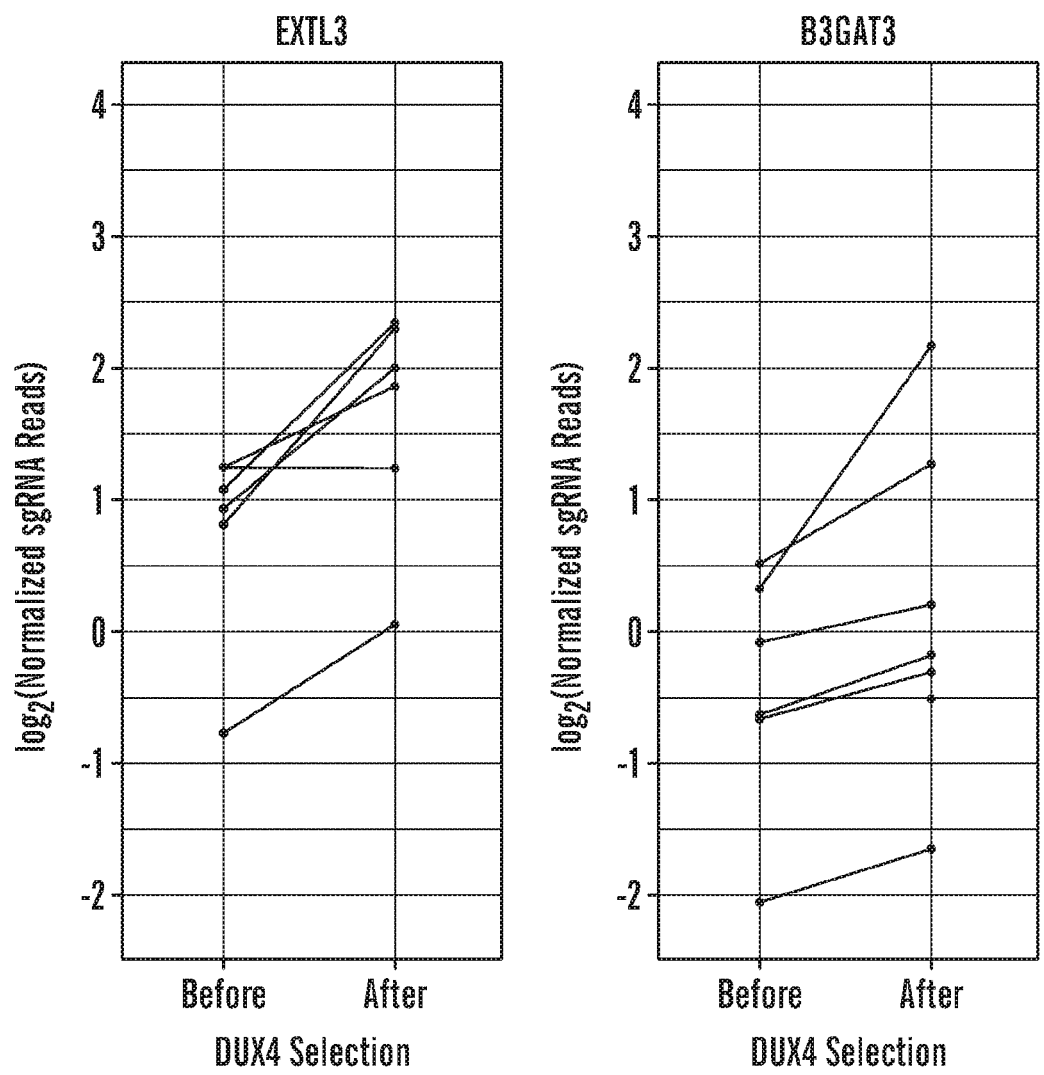
Figure 5:
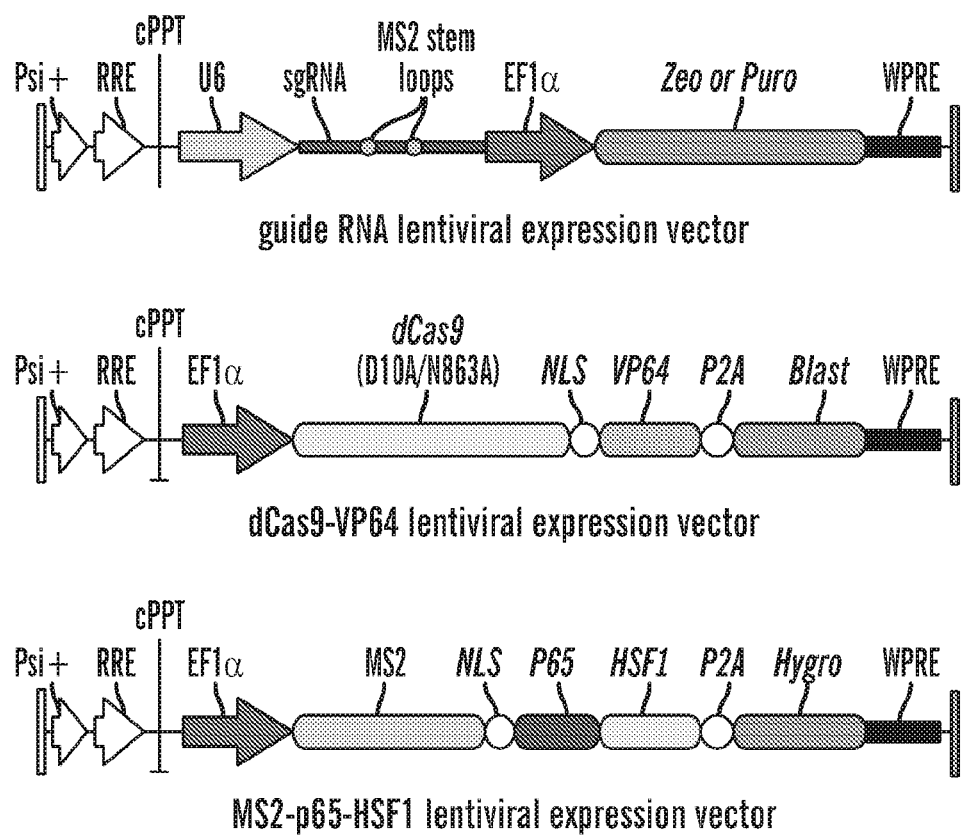
FIG. 5 is a schematic illustrating the structure of lentiviral expression vector (top) for use in CRISPR screening.

FIG. 3A depicts HEK293T cells transduced with the CRISPR LOF library. Wide spread cell death occurs within 48 horns in the gene edited cells transduced with DUX4 baculovirus (FIG. 3B). FIG. 3C shows cells that continued to survive if the harbor gene knock-outs that confer resistance to DUX4 toxicity. FIG. 3D shows cells that grow as colonies. Downstream sequencing and enrichment analysis (FIGS. 4A-4C) was used to identify the CRISPR knock-out target in these cells (FIG. 5). The reproducibility of these genes across multiple independent screens strengthens our confidence in their biological significance in the context of this assay (Table 1).

TABLE 1

Enriched genes ($p < 0.025$) across three screen replicates.

| Gene | Function |
| --- | --- |
| WDR65 | Unknown |
| B3GAT3 | Glycosaminoglycans biosynthesis |
| RPRML | Unknown |
| SLC35B2 | Transmembrane transporter, signal transducer |
| EIF5A2 | mRNA binding protein, regulator of apoptosis |
| EXTL3 | Heparan sulfate biosynthesis |
| MUSTN1 | Embryonic nuclear protein, muscle regeneration and development. |
| TMEM165 | Glycosylation. Calcium transporter. |
| EXT1 | Heparan sulfate biosynthesis |

Many of the candidate genes have been validated, and were studied in functional follow-up in: a) a myogenic cell model; b) DUX4 zebrafish model; and c) whole-genome sequencing data of FSHD families. Known virus uptake genes (B3GAT3 (Beta-1,3-Glucuronyltransferase 3), SLC35B2 (Solute Carrier Family 35 Member B2), B4GALT4 (Beta-1,4-Galactosyltransferase 4)) emerged as significant hits in the loss-of-function screen (Rosmarin et al. 2012). The presence of these 'virus uptake' genes in the list suggests that their loss-of-function may have impeded the uptake of DUX4 baculovirus to enable survival, and thus serves as positive controls for our experimental method.

Example 2: CRISPR Loss-of-Function Screening in MB135 Cells

Figure 9:
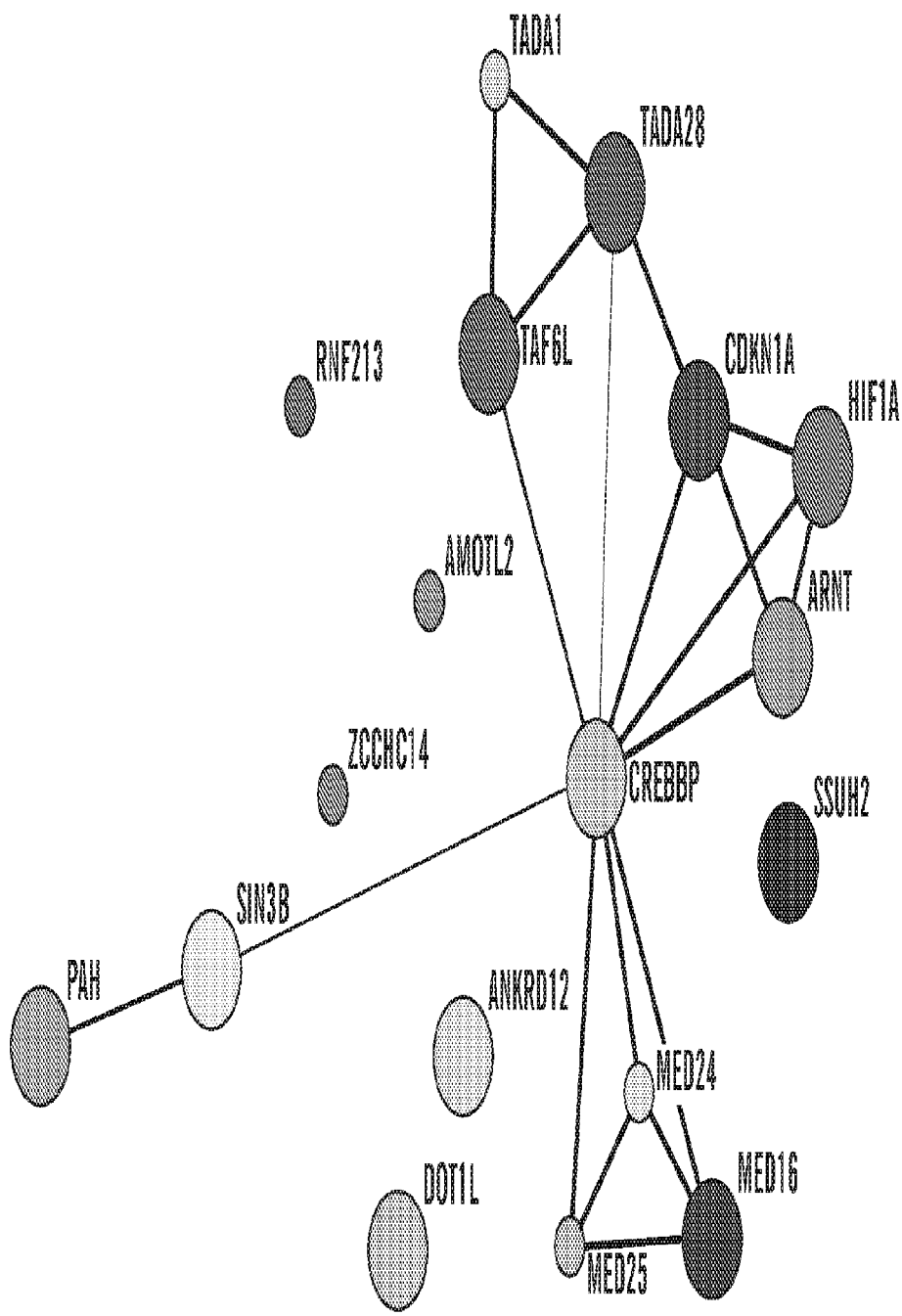
FIG. 9 is a schematic showing members of a hypoxia response pathway, including ARNT=HIF1b, CDKN1A=p21, and CREBBP=CBP that are implicated in FSHD pathogenic process.
Figure 10:
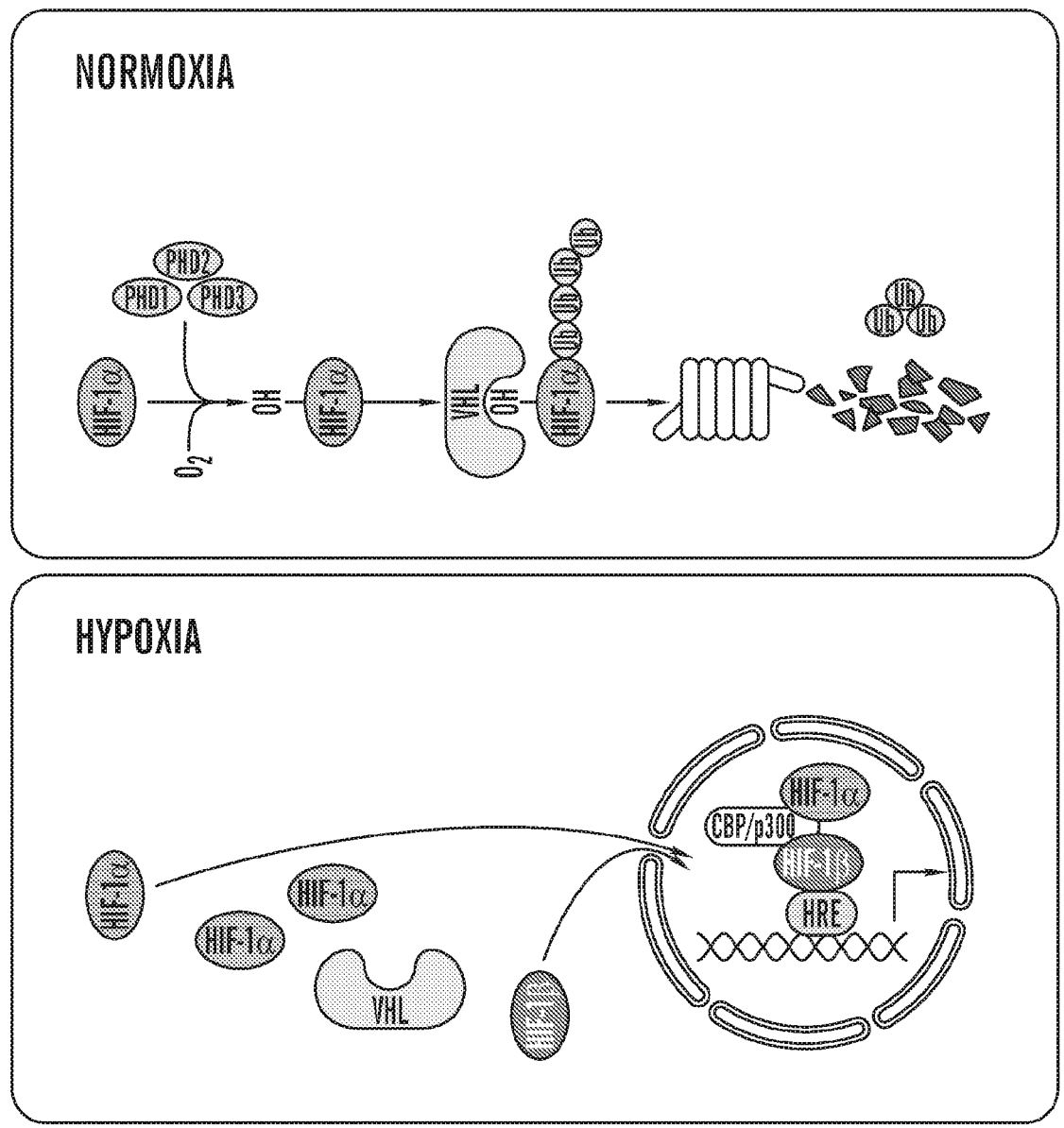
FIG. 10 is a schematic diagram showing the role of HIF-1 alpha in normoxic and hypoxic cells.
Figure 11:
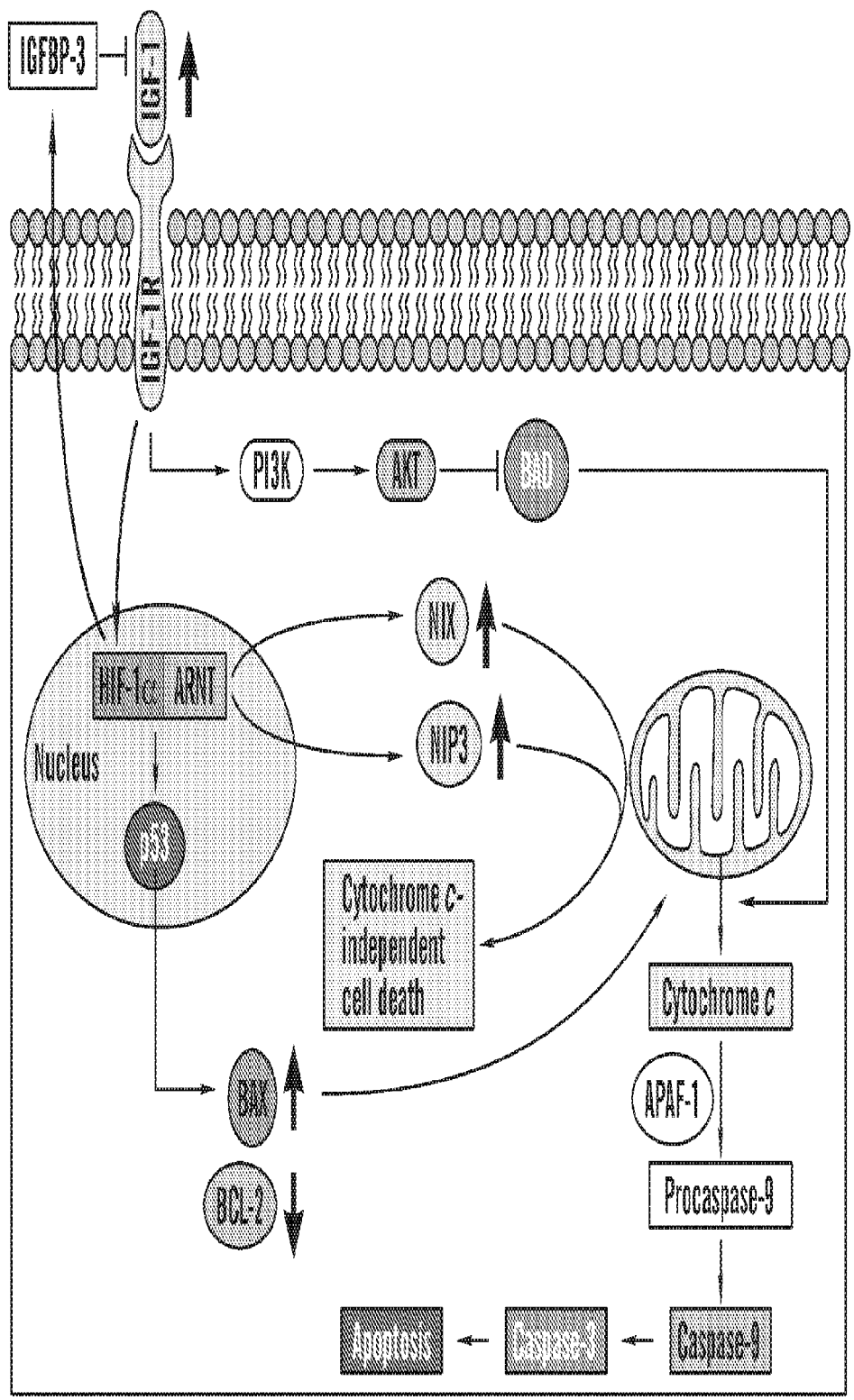
FIG. 11 is a schematic diagram showing that the hypoxic response can lead to apoptosis in cells.

Further CRISPR loss-of-function screening was carried out in HEK293T cells and DUX4 was expressed using a baculovirus expression system. This screening identified the genes shown in FIG. 6. CRISPR loss-of-function screening was also carried out in MB135 cells in which DUX4 expression was induced by doxycydine (FIG. 8B). These screens identified different datasets (FIGS. 6, 7). The MB135 LoF screen identified genes implicated in the hypoxia pathway (FIGS. 9, 10), including ARNT, HIF1b, CDKN1A, p21, CREBBP, and CBP. The hypoxia response pathway is associated with apoptosis (FIG. 11).

Figure 12:
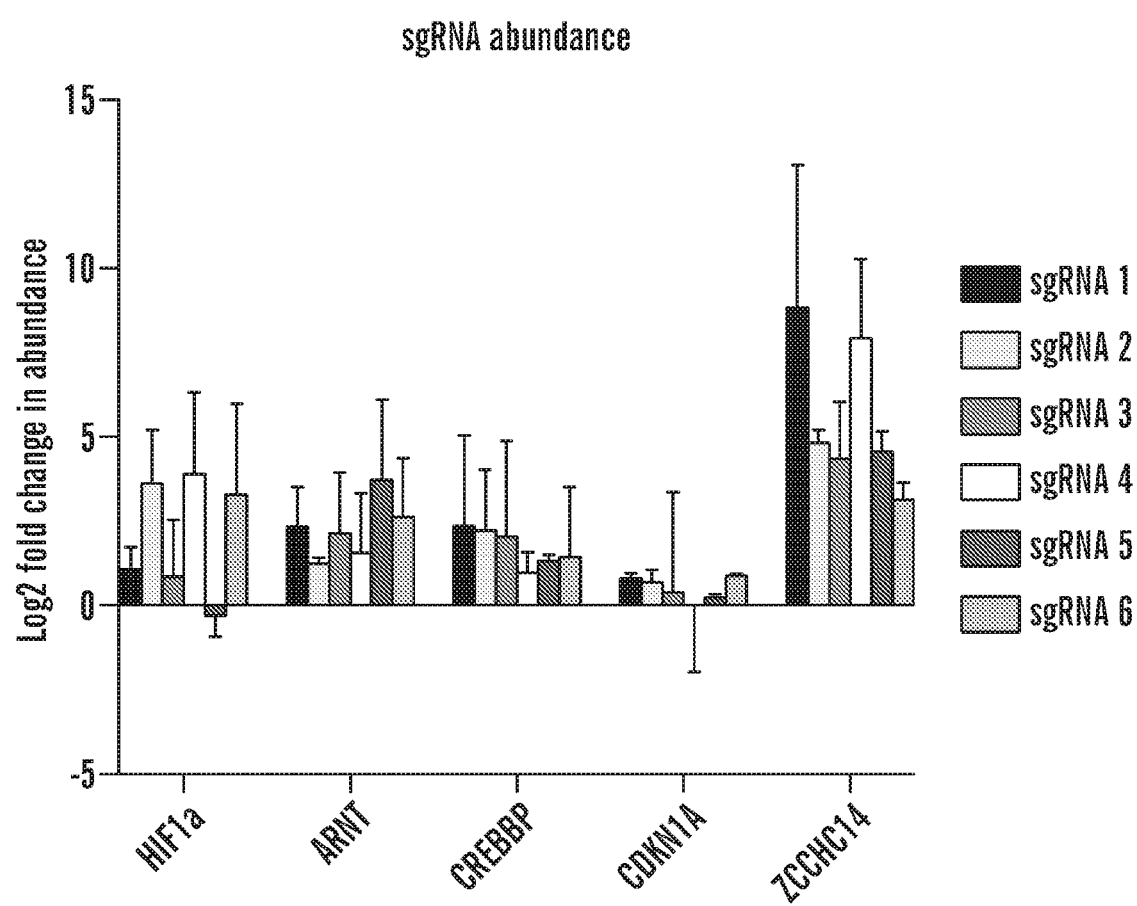
FIG. 12 is a graph showing the change in abundance of sgRNAs in knock-outs of the specified gene.
Figure 13:
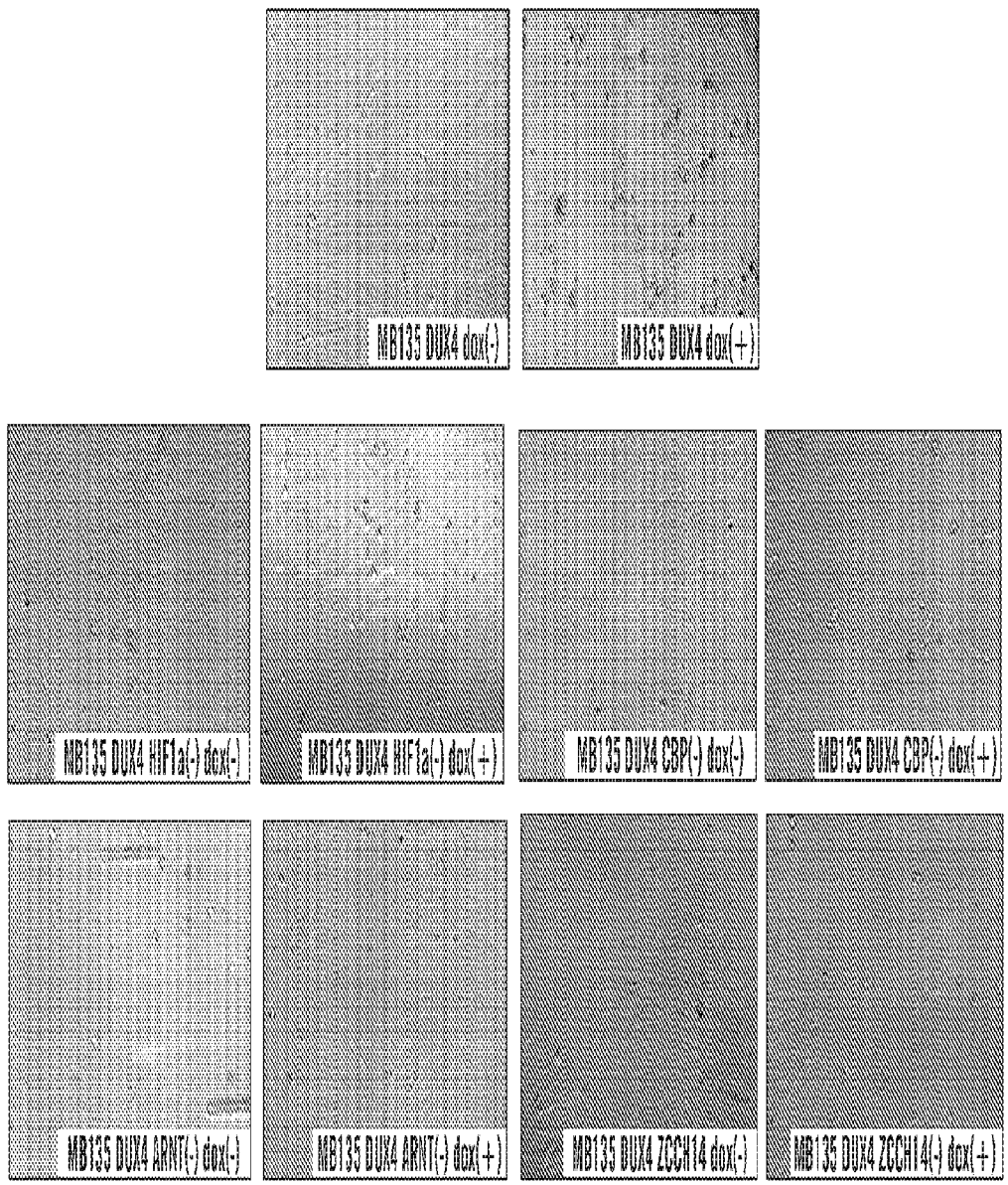
FIG. 13 provides a series of micrographs showing that the single gene knock-outs are resistant to Dux4 induced toxicity.
Figure 14A:
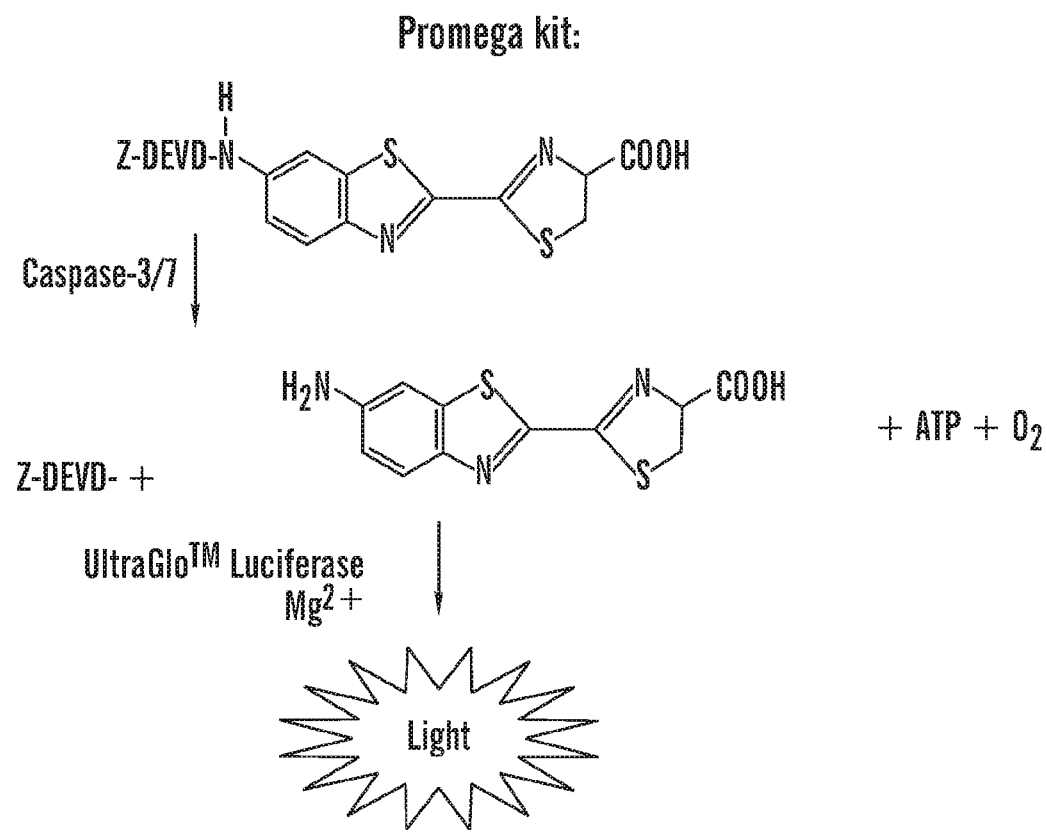
FIGS. 14A and 14B illustrate a method for assaying cell death.
Figure 14B:
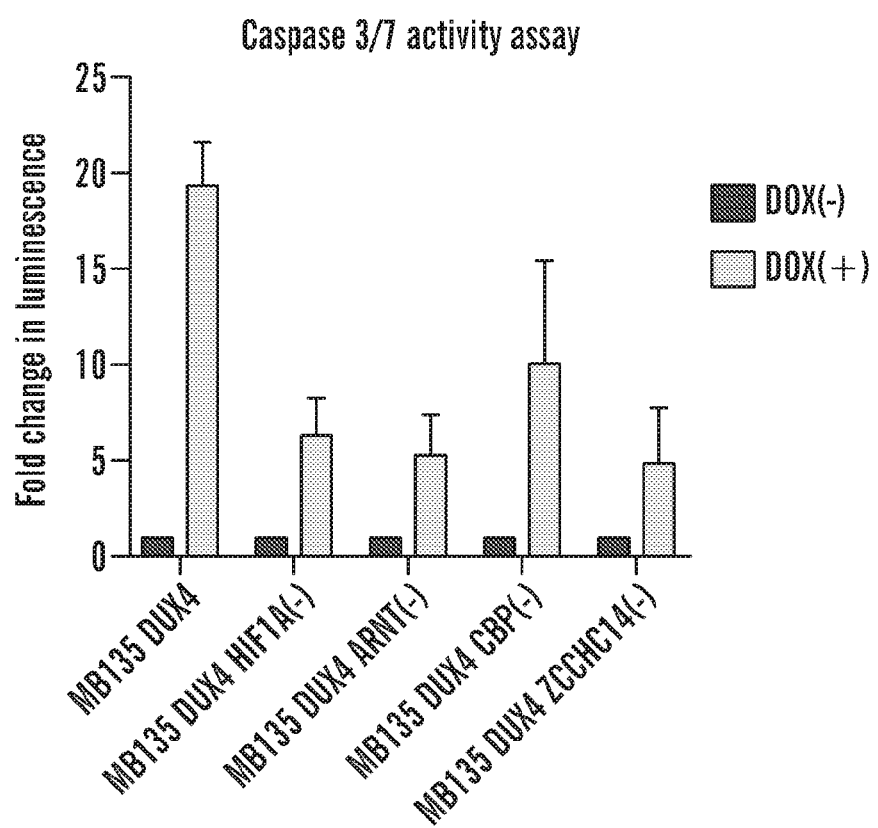
Figure 15A:
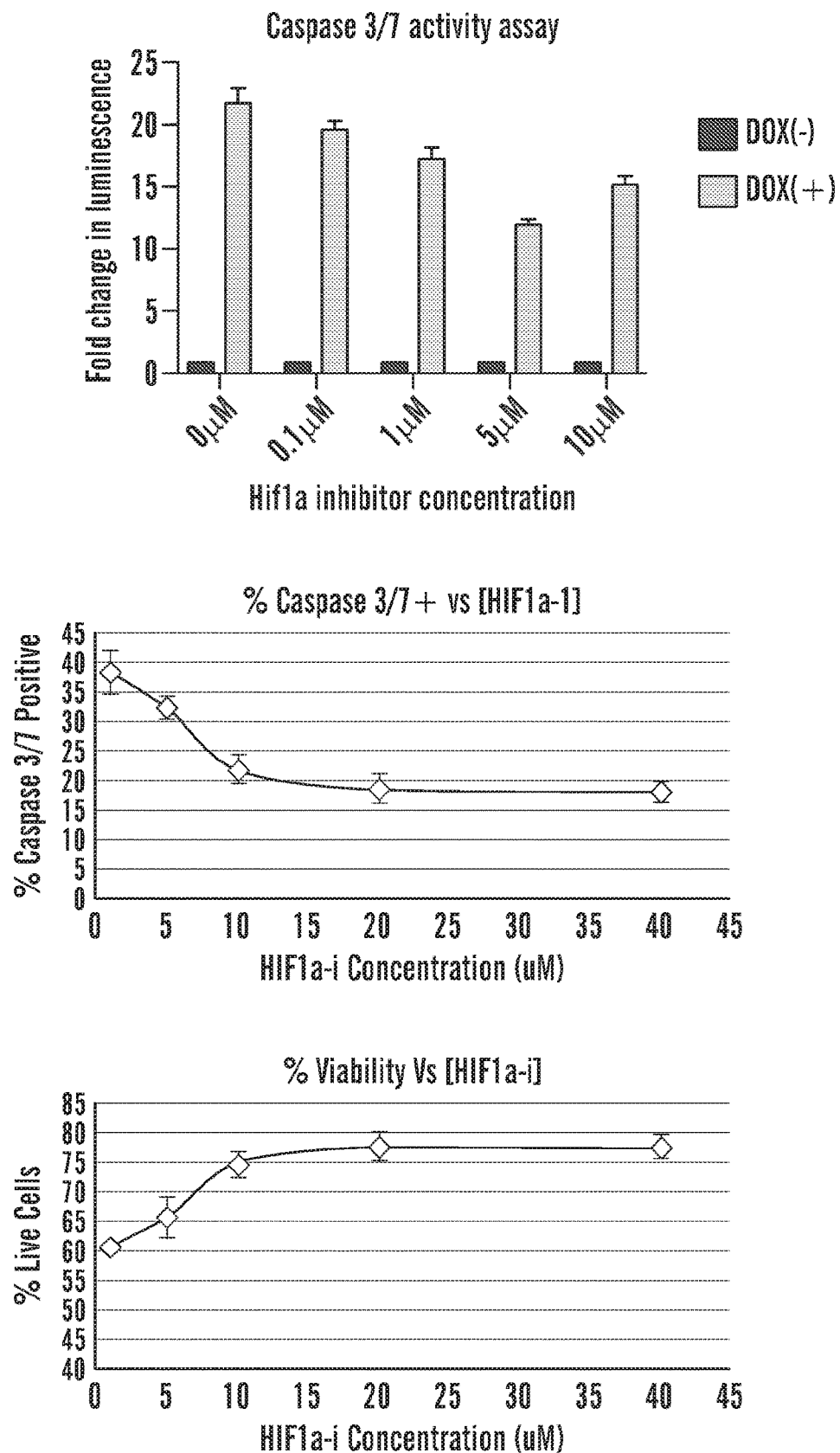
FIG. 15A includes graphs showing the effect of Hif1alpha inhibitor (Santa Cruz) on Caspase 3/7 activity (top panel, bottom left panel) and on cell viability (bottom right panel).
Figure 15B:
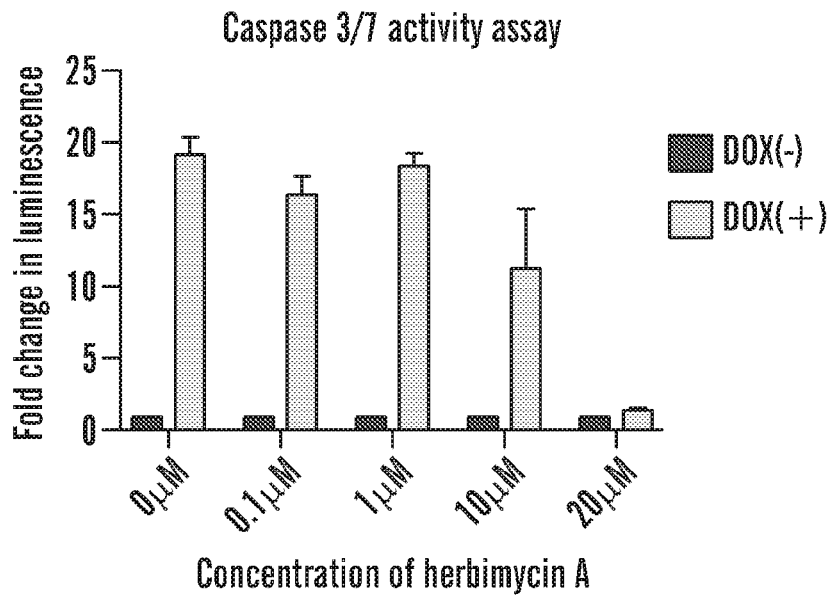
FIG. 15B shows the effect of herbimycin A on Caspase 3/7 activity.

The abundance of sgRNAs in each of the LOF cell lines was measured (FIG. 12). Each sgRNA is specific to the gene. Single gene knock-outs were generated using a lentiCRISPR plasmid. The single gene knock-outs showed comparable DUX4 resistance to that observed in the original CRISPR screening assay (FIG. 13). These results were validated in a Caspase 3/7 activity assay (FIGS. 14A and 14B). To determine whether the results observed with Hif1a knockout could be recapitulated using an inhibitor of Hif1a, experiments with small compound inhibitors were carried out (FIGS. 15A, 15B, 16C, 16D). Results obtained with Herbimycin A showed good suppression of DUX4 toxicity at 20 uM. Herbimycin A is a benzoquinone drug (used for anti-cancer treatment) that binds and inhibits heat shock protein 90 (HSP90) chaperone (tyrosine kinase inhibitor) and is known to deplete dephosphorylated HIF1a. "Dephosphorylated HIF1a may act as the molecular switch that actives the p53-dependent apoptotic pathway under severe hypoxic conditions" (Suzuki Oncogene 2001).

Example 3: FSHD Treated with Anti-Cancer Drugs

Figure 16A:
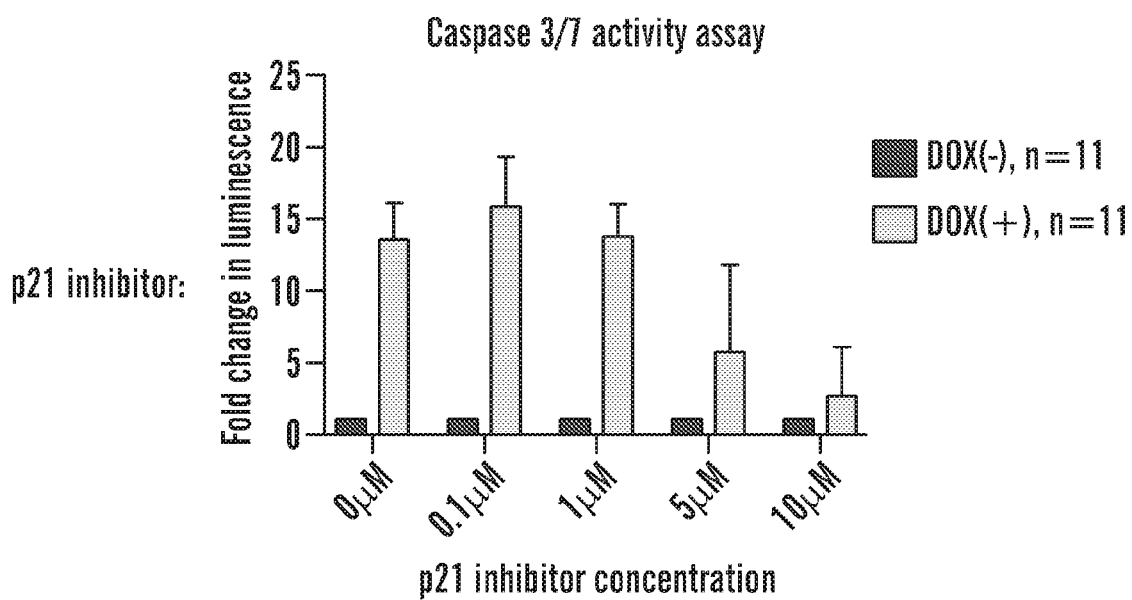
FIG. 16A shows the effect of p21 inhibitor UC2288 on Caspase 3/7 activity.
Figure 16B:
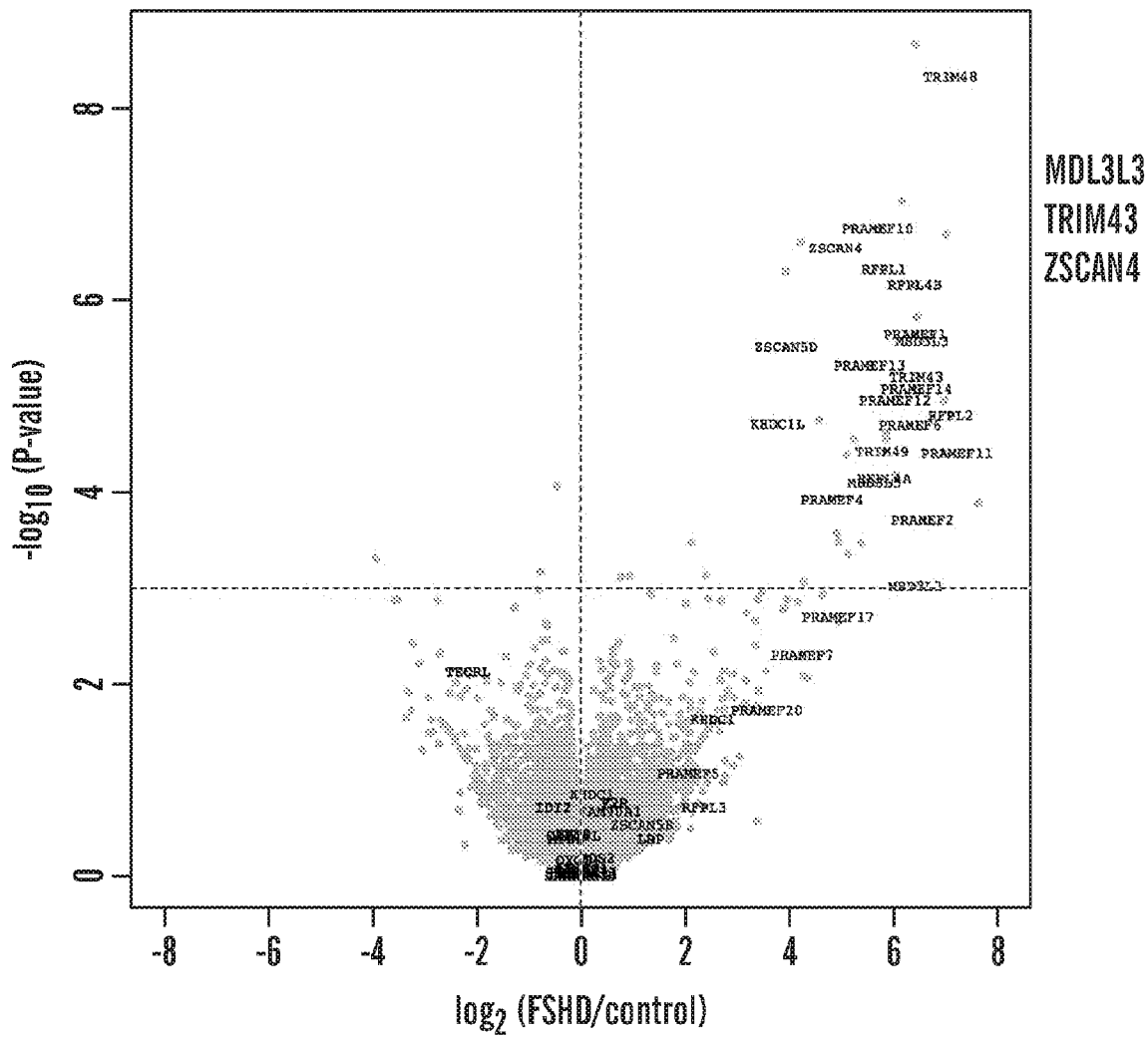
FIG. 16B shows three biomarkers, MDL3L3, TRIM43, and ZSCAN4 associated with FSHD. Levels of these markers can be used to assess the efficacy of FSHD symptoms.
Figure 16C:
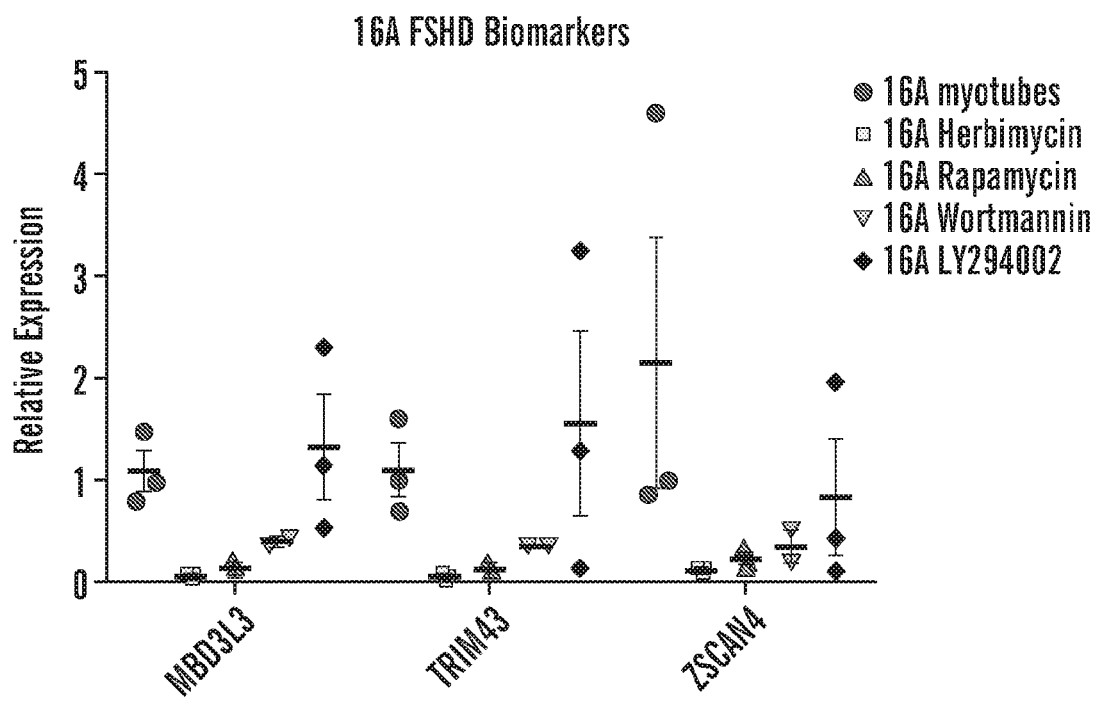
FIG. 16C is a graph showing that markers MDL3L3, TRIM43, and ZSCAN4 can be used to assess the efficacy of drugs that treat FSHD in patient primary myoblast 16A.
Figure 16D:
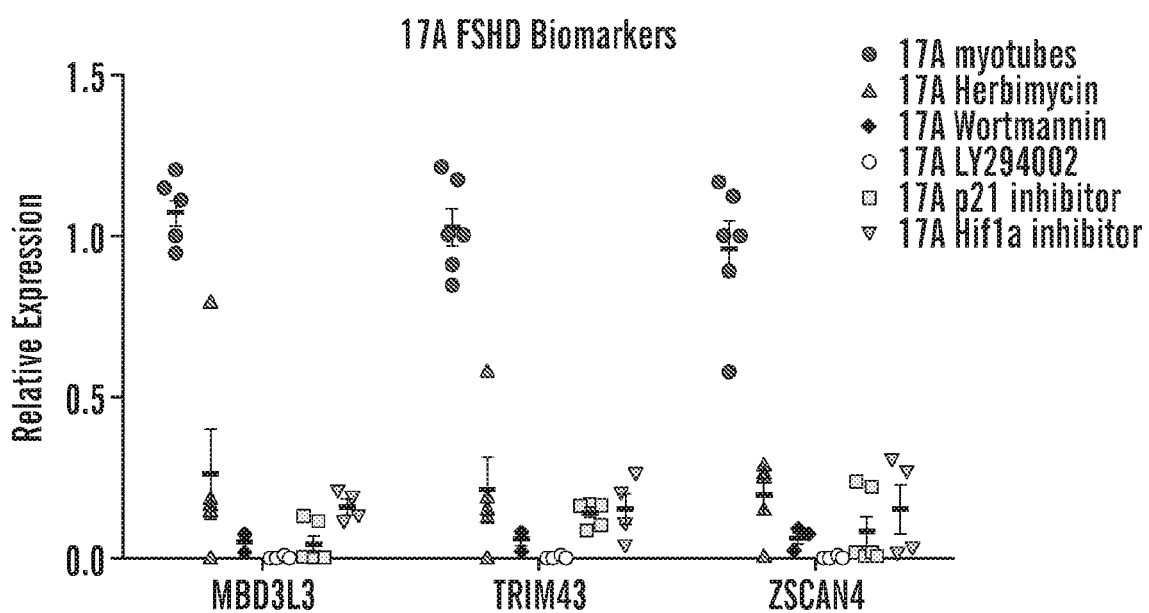
FIG. 16D is a graph showing that the markers MDL3L3, TRIM43, and ZACAN4 can be used to assess the efficacy of drugs that treat FSHD in patient primary myoblast 17A.

One common way to test potential therapies for FSHD is to measure a reduction in FSHD biomarker genes (FIG. 16B). Interestingly, both Hif1a and p21 inhibitors reduced FSHD biomarkers in myotubes isolated from patients 16A and 17A (FIGS. 16C and 16D). Briefly, patient primary myoblasts (17A and 16A) were placed in differentiation media. At day four, drug compounds were added, and myotubes were harvested 24 hours later. RNA extraction and cDNA synthesis was performed. Quantitative real-time PCR for FSHD biomarkers levels of MBDL3L3, TRIM42 and ZSCAN4 was performed. Results indicated a significant reduction in biomarker levels for the majority of drugs tested. This effect showed a Dose-response reduction of biomarkers using Hif1a inhibitor. These results indicate that FSHD can be treated with anti-cancer drugs that target the hypoxia pathway. Anti-cancer drugs useful for treating FSHD are shown in Table 2 (below).

TABLE 2

| Oncogenic signalling inhibitors that also block HIF-1 | | |
|---|---|---|
| Drug | Target | References |
| Herceptin, Iressa, herbimycin | Tyrosine kinases | 112 |
| Calphostin C | Protein kinase C | 112 |
| Wortmannin, LY294002 | PI3K | 113 |
| PD98059 | MAPK | 114 |
| Rapamycin | FRAP/mTOR | 115 |
| Diphenylene iodonium | Redox signalling | 87 |
| Mannoheptulose | Glucokinase | 116 |

FRAP, FKBP/napamycin-associated protein; MAPK, mitogen-acitvated protein kinase; PI3K, phosphatidylinositol 3-OH kinase.

Figure 17A:
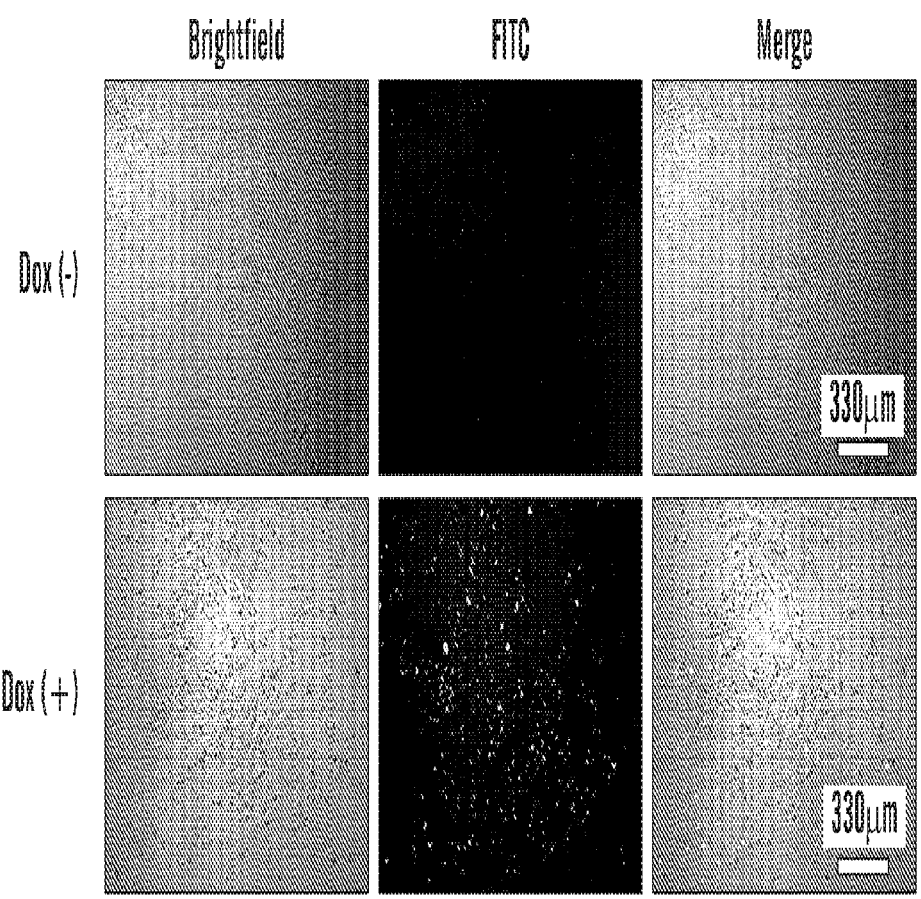
FIGS. 17A to 17E present data generated from cell death assay validation for single knock-outs and drug compounds.
Figure 17B:
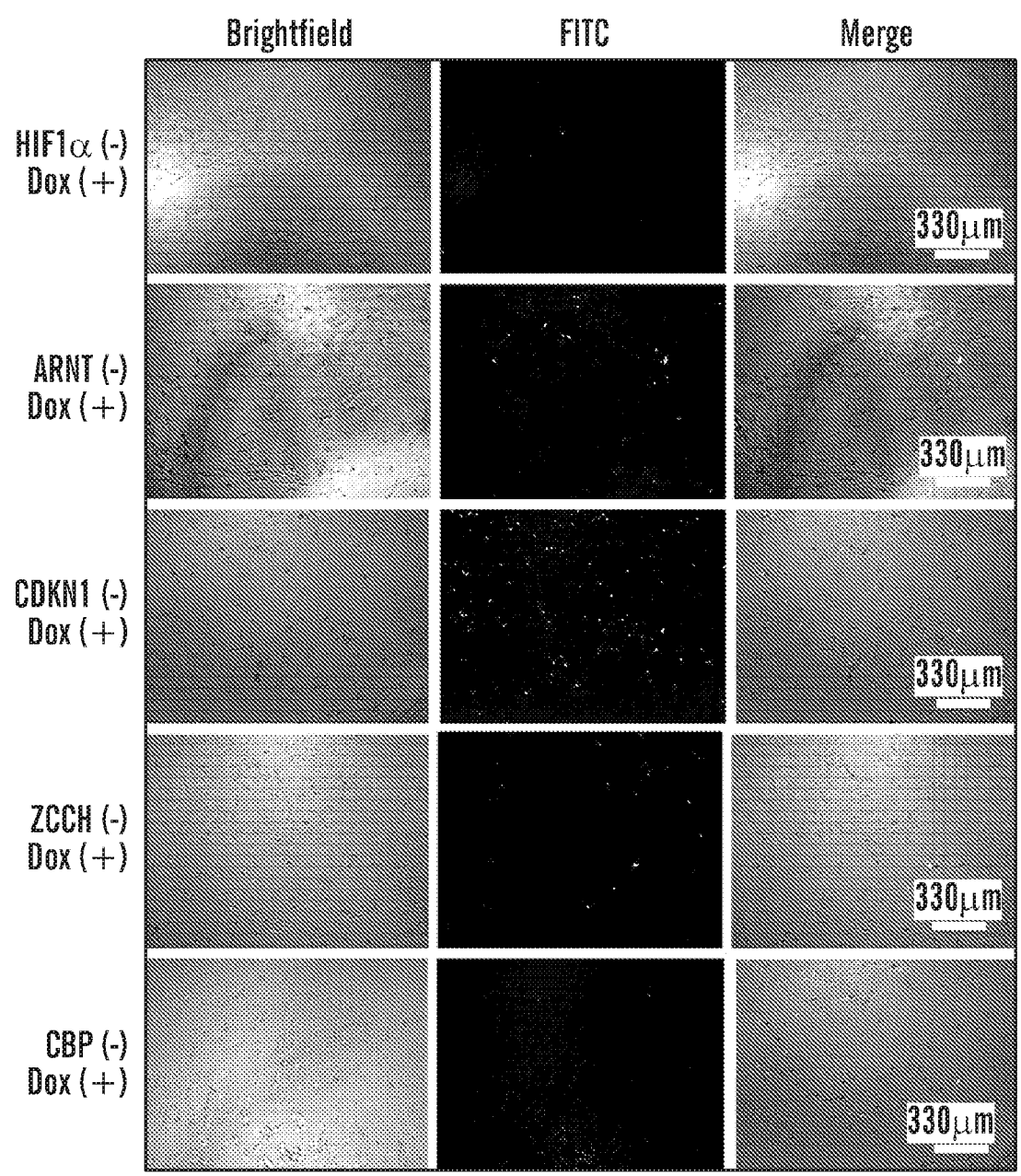
Figure 17C:
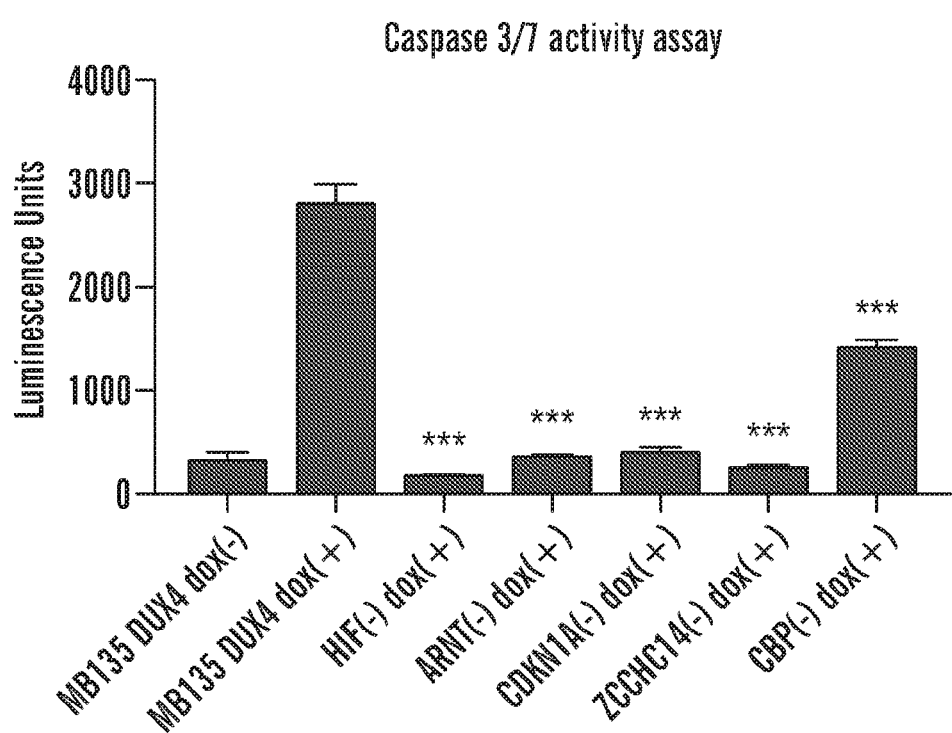
Figure 17D:
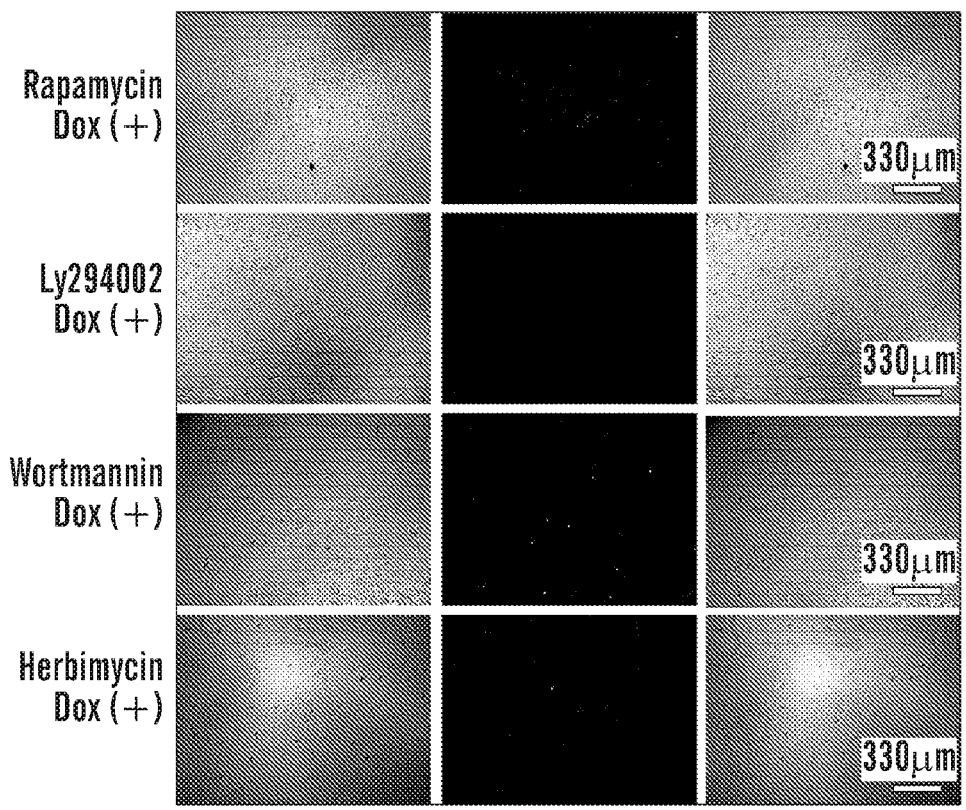
Figure 17E:
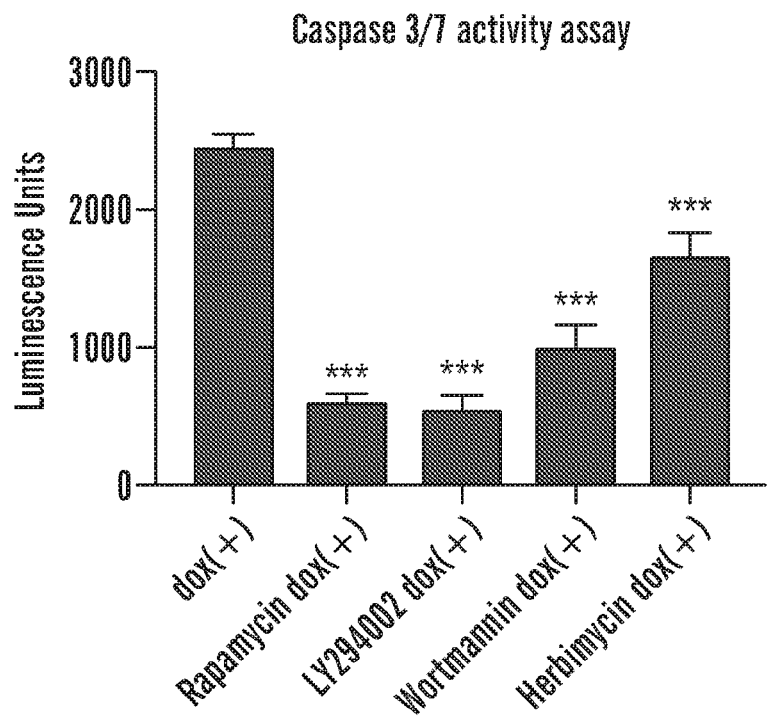

Cell death assay were then used to validate single knockouts cell lines (FIGS. 17A-17C). Caspase fluorescence was visible (FITC) upon 48 hours of doxycydine treatment of DUX4 inducible line (FIG. 17A), and single knock-out lines demonstrated reduced caspase fluorescence after 48 hours of doxycydine treatment (FIGS. 17B and 17C). Selected drug compounds were then tested and demonstrated reduced caspase fluorescence upon 48 hours of doxycydine treatment (FIGS. 17D and 17E), which indicated efficacy of the drug that could be further examined in vivo.

Figure 18A:
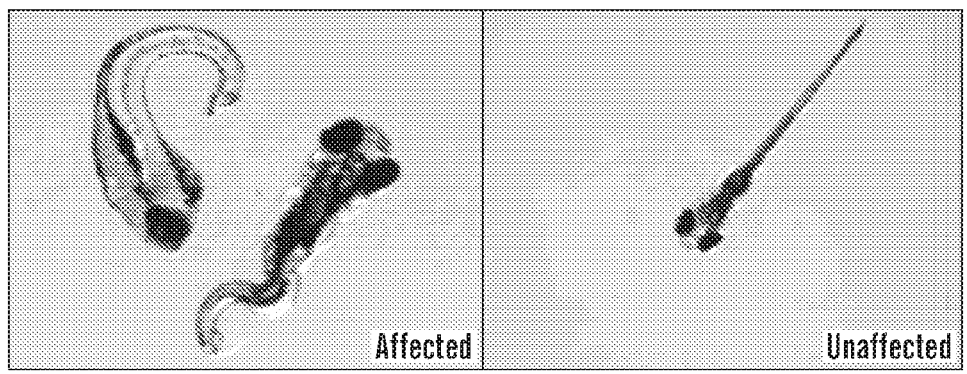
FIG. 18A presents side-by-side comparison of affected and unaffected zebrafish after injection with DUX4.
Figure 18B:
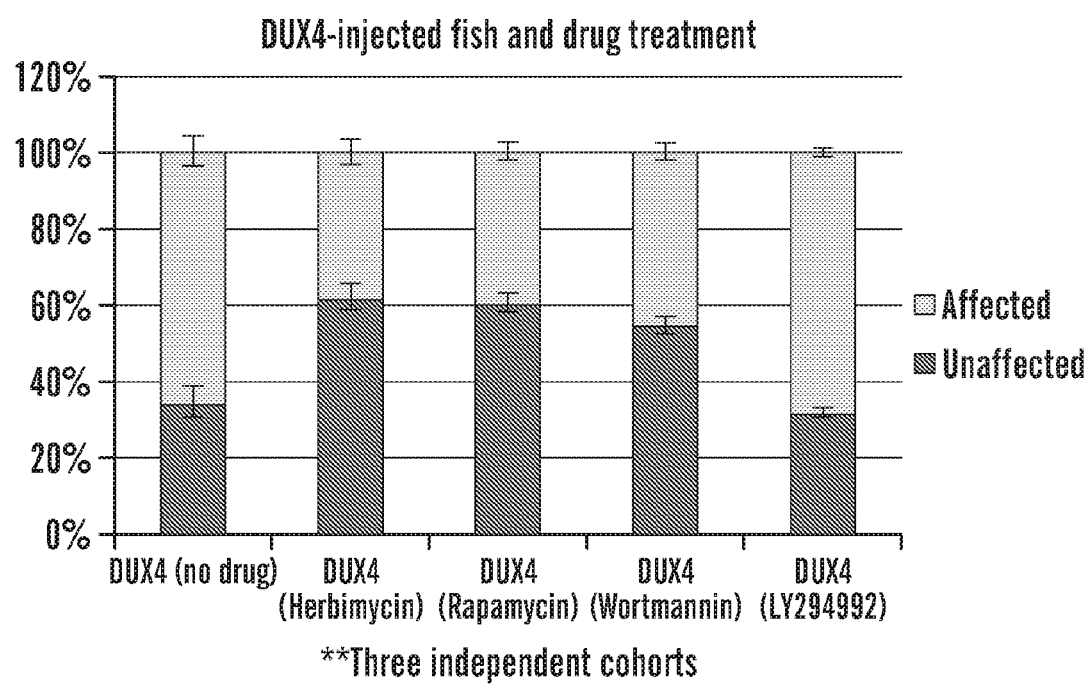
FIG. 18B is a graph showing that the percentage of affected zebrafish was significantly reduced after treatment with herbimycin, rapamycin, or wortmannin significantly reduced the percentage of affected zebrafish compared to control fish that received no drugs or fish that received Ly294002.

Drugs that show efficacy in vitro can be tested in a zebrafish model of FSHD. Measured by caspase 3/7 activity, rapamycin, LY294002, wortmannin, and herbimycin all showed efficacy in vitro that warranted follow-up in vivo testing (FIGS. 16C, 16D, 17D, and 17E). Once the efficacy of efficacy of rapamycin, LY294002, wortmannin, and herbimycin DUX4 was observed in the cell death assay and in patient cell lines, the compounds were then examined to determine if they could alleviate symptoms of DUX4-injected zebrafish. After injecting DUX4 into zebrafish, the test subjects were then treated with the four drug compounds 24 hr post-injection. Injected fish were categorized into affected or unaffected groups based on whole-body phenotype (FIG. 18A). Treatment with herbimycin, rapamycin and wortmannin resulted in significantly decreased percentage of affected fish at day 7 compared to the DUX4-injected no drug control group (FIG. 18B).

Example 4: Identify Genes Whose Gain-of-Function Results in Resistance to DUX4 Toxicity Analogous to the loss-of-function CRISPR screen, a gain-of-function screen was performed using the commercially available SAM (Synergistic Activation Mediator) library consisting of pooled sgRNA lentivirus contructs from AddGene (Konermann et al. 2014) (FIG. 5). In addition to the pooled sgRNA activation library, CRISPR induced transcriptional activation required additional components for the formation of the SAM complex—an inactive Cas9 fused to a transcriptional activation domain (dCas9-VP64) and effector components (MS2-p65-HSF1) (FIG. 5).

Lentivirus constructs for each component of the complex must be amplified and packaged into lentivirus particles. Prior to transduction with the pooled sgRNA library, we first established a population of cells with stable integration of both dCas9-VP64 and MS2-p65-HSF1 constructs that have been transduced undergone antibiotic selection. This population was subsequently transduced with the sgRNA activation library at a low MOI (0.3) to reduce the probability of cells taking up more than 1 sgRNA. Similar to our loss-of-function screen, transduction of 500 cells per guide is optimal, and this representation was maintained over the 7-day antibiotic selection process. See FIG. 2C for an experimental flow diagram. DUX4 toxicity in cells can be used as a positive selective pressure to isolate cell populations that harbor activated genes that render them resistant to DUX4.

Example 5: CRISPR-Mediated Upregulation of DUX4 Modifier Genes

To induce DUX4 toxicity in culture, optimal DUX4 baculovirus titers were determined that yield the most consistent and reproducible levels of widespread cell death within 48 hours. Cells carrying a CRISPR-induced gain-of-function mutation in a DUX4 modifier gene remained viable and continued to proliferate after 48 hours of DUX4 induction, thus giving rise to more DUX4 'resistant' daughter cells for subsequent sequencing analysis, similar to the 'resistant' colonies in the loss-of-function screen.

Genes whose upregulation results in resistance to DUX4 toxicity were identified as follows. Genomic DNA was isolated from two populations of cells for comparison: 1) population of gene-edited cells without DUX4 over-expression; 2) population of gene-edited cells that are 'resistant' to DUX4 over-expression. A PCR reaction was performed to amplify sgRNA sequences from these populations and to also attach experimental barcodes and Illumina sequencing primers. The resulting amplicons were sequenced using the Illumina Next-seq platform.

Genes that emerged as significant from the gain-of-function screen were identified by the following criteria: 1) significantly enriched levels after DUX4 selection; 2) multiple sgRNA targets arise from the same gene; 3) meaningful functional annotation of gene; 4) known DUX4 transcriptional targets; 5) availability of Taqman probes. Genes that fulfill these criteria will be subject to further validation and follow-up in both in vitro and in vivo models. Validation of candidate genes in myoblast lines was carried out. Individual CRISPR gain-of-function lines of the candidate genes using immortalized human myoblast cells were generated (MB135) (Yao et al. 2014). Similar to the process of generating individual CRISPR knock-out cells for validation of our loss-of-function screen hits, this process involved choosing sgRNA sequences that demonstrate enrichment in the screen, and cloning into the same lentiviral backbone used for the pooled library). This lentivirus was then packaged and transduced into myoblasts stably expressing dCas9-VP64 and MS2-p65-HSF1. The gain-of-function mutation is reproduced independent of the sgRNA library used in our screen. Individual gain-of-function lines were tested for resistance to DUX4 cell death using multiple lines of evidence such as caspase-3/7 fluorometric assays and TUNEL immunofluorescence assays.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for suppressing DUX4 toxicity in a cell, the method comprising contacting a cell overexpressing DUX4 with an agent that reduces the expression or activity of a hypoxia response pathway protein selected from the group consisting of hypoxia-inducible factor 1-alpha (HIF1A), hypoxia-inducible factor 1-beta (HIF1B), aryl hydrocarbon receptor nuclear translocator (ARNT), CREB binding protein (CREBBP), CBP, and zinc finger CCHC-type containing 14 (ZCCHC14), wherein the agent is Herbimycin A, Herceptin, Iressa, calphostin C, wortmannin, LY294002, PD98059, rapamycin, diphenylene iodonium, mannoheptulose, 4-Chloro-3-(trifluoromethyl)phenyl isocyanate (CAS 327-78-6), Sterigmatocystin, Chetomin, Cryptotanshione, EF-24, FM19G11, and PX 12.

* * * * *